(12) United States Patent
Sun et al.

(10) Patent No.: US 8,010,176 B2
(45) Date of Patent: Aug. 30, 2011

(54) METHOD FOR ELASTOMAMMOGRAPHY

(75) Inventors: Lizhi Sun, Irvine, CA (US); Yi Liu, Indianapolis, IN (US); Zhiguo Wang, Iowa City, IA (US); Ge Wang, Blacksburg, VA (US)

(73) Assignee: The Regents of the University of California, Oakland, CA (US)

( * ) Notice: Subject to any disclaimer, the term of this patent is extended or adjusted under 35 U.S.C. 154(b) by 1187 days.

(21) Appl. No.: 11/731,624

(22) Filed: Mar. 30, 2007

(65) Prior Publication Data

US 2007/0238966 A1 Oct. 11, 2007

Related U.S. Application Data

(60) Provisional application No. 60/744,009, filed on Mar. 30, 2006.

(51) Int. Cl.
*A61B 5/00* (2006.01)
(52) U.S. Cl. ........ 600/407; 600/425; 600/473; 382/128; 382/131; 382/132; 378/37
(58) Field of Classification Search .................. 600/425, 600/407, 473; 382/128, 131, 132; 378/37
See application file for complete search history.

(56) References Cited

U.S. PATENT DOCUMENTS

| 2003/0123720 | A1* | 7/2003 | Launay et al. | 382/132 |
|---|---|---|---|---|
| 2003/0171672 | A1* | 9/2003 | Varghese et al. | 600/420 |
| 2004/0234113 | A1* | 11/2004 | Miga | 382/128 |
| 2005/0096515 | A1* | 5/2005 | Geng | 600/315 |
| 2005/0283076 | A1* | 12/2005 | Hangiandreou et al. | 600/443 |

OTHER PUBLICATIONS

Oberai et al., Phys. Med. Bio., 49, 2004, pp. 2955-2974.*
Liu et al., Med. Phys., 31, (6), Jun. 2004, pp. 1322-1332.*
Oberai, A., Evaluation of the adjoint equation based algorithm for elasticity imaging, Phys. Med. Biol. 49 p. 2955-2974 (2004).*
Liu, W., Elastographic versus x-ray CT imaging of radio frequency ablation coagulations: An in vitro study, Med. Phys. 31 No. 6 pp. 1322-1332, (Jun. 2004).*

* cited by examiner

*Primary Examiner* — Ruth S Smith
*Assistant Examiner* — Rajeev Siripurapu
(74) *Attorney, Agent, or Firm* — Marcus C. Dawes; Daniel L. Dawes

(57) ABSTRACT

A method for obtaining a distribution of a stiffness property in tissue includes applying a plurality of loadings to the tissue, obtaining a plurality of two-dimensional (2-D) imaging projections of the tissue from different directions, measuring a force resulting from one of the plurality of loadings, measuring from at least one of the plurality of 2-D imaging projections a displacement of the tissue in response to the force, obtaining an initial set of input parameters for an estimated stiffness property of the tissue, and solving iteratively for the stiffness property using a computer.

13 Claims, 16 Drawing Sheets

METHOD FOR ELASTOMAMMOGRAPHY

CROSS-REFERENCE TO RELATED APPLICATIONS

The present application claims benefit of U.S. provisional application No. 60/744,009, filed Mar. 30, 2006.

BACKGROUND OF THE INVENTION

1. Field of the Invention

The invention relates generally to medical imaging technology and more particularly to breast cancer diagnosis using the measurement and display of tissue stiffness properties.

2. Description of the Prior Art

X-ray mammography is the primary method for early detection of breast cancers. According to the reports of US Food and Drug Administration, mammography can diagnose 85 to 90 percent of the breast cancers in women over the age of 50, and can detect a lump up to two years before it can be sensed by manual palpation. While it is easier to detect malignancies as age increases and the breast tissue becomes more fatty, mammography fails to detect small cancers in dense breasts. Further, mammography may not be specific in terms of tumor benignity and malignancy, especially when the breast tissue is radiodense. A significant number of suspicious masses referred by mammography for surgical breast biopsy are, in fact, benign. False-positive mammograms induce anxiety, distress and emotional disruption in patients.

It has been well recognized that the tissue stiffness plays an important role in diagnosis of breast cancers, as tumors are stiffer than the surrounding breast tissues, and malignant tumors are much stiffer than benign ones. In other words, in vivo identification of the elastic moduli of normal and abnormal breast tissues, which describe the stiffness, should improve the accuracy for breast-cancer diagnosis.

There have been elastography studies based on ultrasound or MRI breast imaging. Developed in 1990s by Ophir (Ophir, J. et al., 1999, "Elastography: ultrasonic estimation and imaging of the elastic properties of tissues," *Proceedings of the Institution of Mechanical Engineers, Part H: Journal of Engineering in Medicine*, vol. 213, no. 3, pp. 203-233), ultrasound elastography (USE) was the first modulus-imaging modality. Although capable of providing new information on detecting pathological tumors, USE suffers from limitations in the detectable stiffness range which is imposed by the minimum resolvable wavelength. Most USE elastograms are referred to as the strain imaging, which may not always provide useful information on the locations and characterizations of heterogeneous lesions. For example, the phenomenon known as "butterfly wings" (Ophir et al. 1999) is frequently observed in the USE strain elastograms, which may be misleading with respect to tumor detection.

Magnetic resonance elastography (MRE) was developed more recently as the second-generation elastography modality. MRE is capable of producing adequate spatial and contrast resolutions. It is, however, a high cost MR imaging procedure, making it less practical for many patients. In addition, the penetration depth of shear waves within organic tissue is limited to only a few centimeters. Due to a large frequency-dependent attenuation, only low-frequency waves of about 50-100 Hz are usable. This limits the spatial resolution and the achievable detectability of small lesions.

Thus, new approaches of elastography are still needed to achieve quick, low-cost, and low-dose screening and diagnosis of breast cancers.

BRIEF SUMMARY OF THE INVENTION

The illustrated embodiment of the invention is a method for obtaining a distribution of a stiffness property in tissue comprising the steps of applying a plurality of loadings to the tissue, obtaining a plurality of two-dimensional (2-D) imaging projections of the tissue from different directions, measuring a force resulting from one of the plurality of loadings, measuring from at least one of the plurality of 2-D imaging projections a displacement of the tissue in response to the force, obtaining an initial set of input parameters for an estimated stiffness property of the tissue, and solving iteratively for the stiffness property using a computer.

In accordance with another embodiment of the invention, the invention is directed to a computer readable medium containing instructions, where the instructions include: inputting an initial set of estimated parameters characterizing tissue stiffness property to a tissue model, measuring from a two-dimensional imaging projection a displacement of the tissue in response to a force, obtaining a finite-element representation for the displacement and the force, solving iteratively for the stiffness property, and outputting a suggestion for tumor characterization in the tissue based on the iteratively solved stiffness property.

In accordance with another embodiment of the invention, an apparatus for screening cancerous tumor in tissue includes a mammography device for generating a plurality of two-dimensional imaging projections, means for applying a loading to the tissue, means for measuring at least one of a force and a displacement due to the loading, a computer for iteratively solving a distribution of a stiffness property of the tissue, and means for outputting a suggestion to a health care provider based on the solved stiffness property.

While the method and apparatus have been or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

Figure 1:
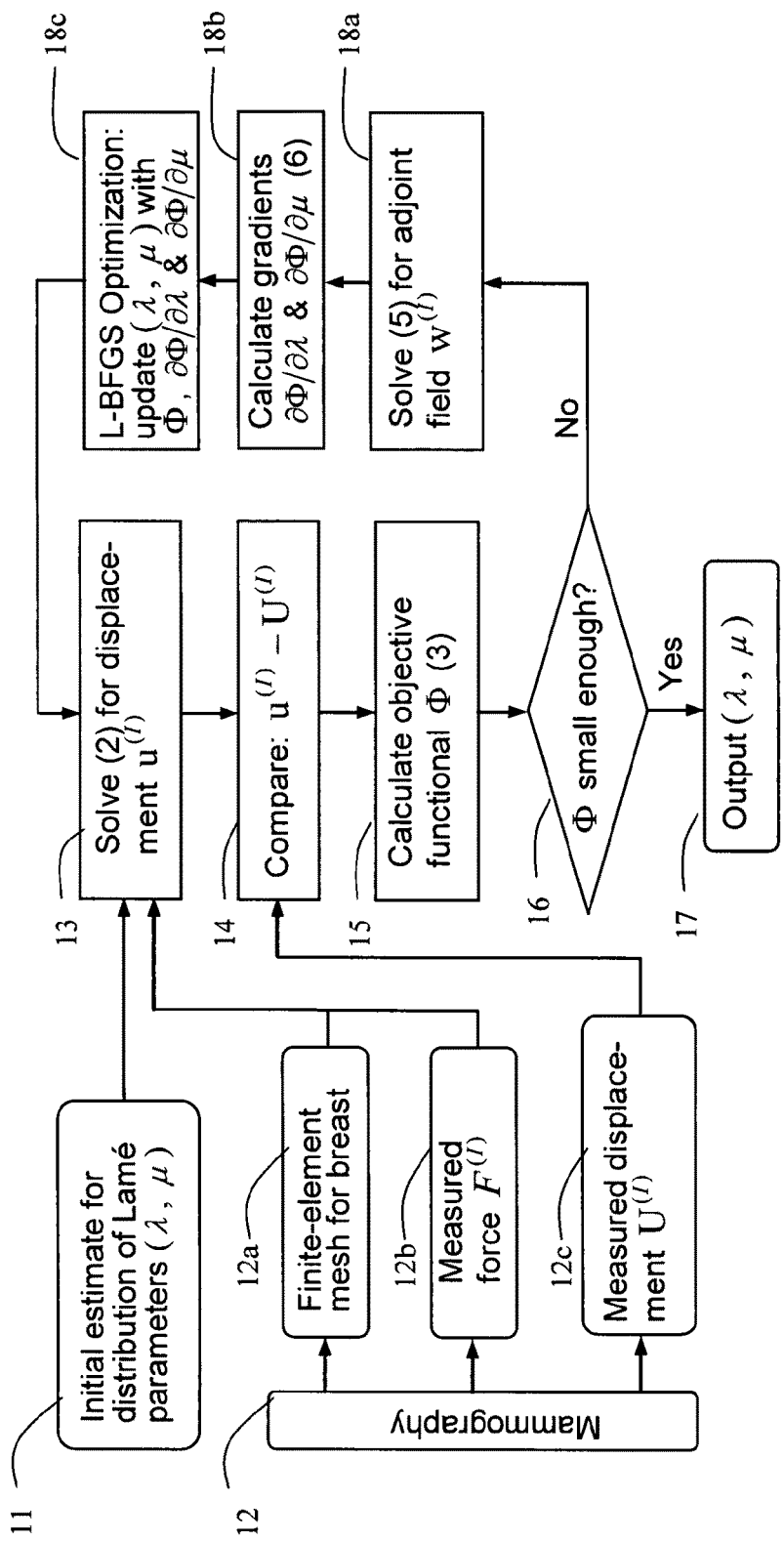
FIG. 1 is a flowchart illustrating an elastomammography method in accordance with an embodiment of the invention.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION

Existing imaging modalities, such as X-ray mammography, ultrasound, and MRI, are not quite specific enough in terms of tumor benignity and malignancy. The illustrated embodiments of the invention provide a new imaging modality framework. Although the method and apparatus described below are referred to as elastomammography, and are described in terms of generating elastograms of breast tissues based on X-ray mammography in exemplary cases, it is noted that the invention may also include other imaging methods and other regimes of spectra, such as computed tomography (CT), and infrared imaging. In addition, embodiments of the invention may apply to types of cancer screening other than breast cancers.

The illustrated embodiments of the invention can provide higher specificity than using conventional mammography alone for breast cancer screening, characterization, differentiation, diagnosis and follow-ups, as cancerous, benign, and normal tissues may be better characterized and differentiated using elastomammography. The fundamental principle is that the elastic responses of lesion masses are substantially different from those of the surrounding tissues.

In accordance with an embodiment of the invention, displacement information is measured from two-dimensional imaging, e.g., mammography projections before and after breast compression. Incorporating the displacement measurement, an elastography reconstruction algorithm is used to estimate the elastic moduli of heterogeneous breast tissues.

The theory, algorithm, and sample studies of elastomammography are described below. A method in accordance with an embodiment of the invention is described with respect to FIG. 1.

In step 11, an initial estimate of Lamé parameters $\lambda$ and $\mu$ is obtained. The Lamé parameters $\lambda$ and $\mu$ are material properties relating stress to strain, and are functions of spatial locations x. A mammography is performed in step 12. A finite-element mesh for the breast is built in step 12a. A force $F^{(I)}$ is measured in step 12b, and a displacement $U^{(I)}(x)$ in response to the force $F^{(I)}$ is measured in step 12c. Results from steps 11, 12a and 12b are input into equation (2), described below, to solve a displacement $u^{(I)}(x)$ in step 13. In step 14, the calculated displacement $u^{(I)}(x)$ from step 13 is compared with the measured displacement $U^{(I)}(x)$ from step 12c. In step 15, the objective function $\Phi$ is calculated based on $u^{(I)}(x)$ and $U^{(I)}(x)$ using equation (3). The objective function $\Phi$ is evaluated in step 16. If $\Phi$ is smaller than a predetermined threshold (as determined by a conventional accuracy requirement, e.g., requiring the final output to be accurate to within a few percent), the parameters ($\lambda$, $\mu$) are output in step 17 and are further used for diagnostics purposes. If the objective function $\Phi$ is not satisfactorily small, equation (5), described below, is solved in step 18a for the adjoint displacement field $w^{(I)}$. In step 18b, the gradients of the objective function $\Phi$ are calculated using the following equation (6), and the input ($\lambda$, $\mu$) values are updated in step 18c. Steps 13-16 are then repeated using the updated $\lambda$ and $\mu$ values.

The algorithms of the invention and the equations used in FIG. 1 are now described in detail using exemplary cases. For exemplary purposes, the mechanical properties of normal breast tissue and tumors are assumed to be linearly elastic and isotropic; i.e., they are described with elastic Lamé parameters $\lambda$ and $\mu$.

Typical clinical mammography applies M ($\geq 2$) individual compressions on the breast so that the maximum amount of tissue can be imaged and examined from different view angles. Information about the displacements is collected from projective images, and is used in the elastomammography for identifying the Lamé parameters of the tissues.

The three-dimensional (3-D) reconstruction algorithm for Lamé parameters is optimization-based. The displacement and force (loading) quantities with the I-th experiment are denoted with superscript "$(I)$". Denoting for the I-th loading the measured displacement field in the biomedical medium of interest ($\Omega$), e.g., an area of breast tissues, as $U^{(I)}(x)$, and the calculated displacement field associated with the trial values of Lamé parameters ($\lambda(x)$, $\mu(x)$) as $u^{(I)}(x)$, the elastomammography seeks Lamé parameters such that the following objective function $\Phi(\lambda(x), \mu(x))$ is optimally minimized:

$$\Phi(\lambda(x), \mu(x)) = \sum_{I=1}^{M} \int_{\Omega} (u^{(I)}(x) - U^{(I)}(x)) \cdot \chi^{(I)}(x) \cdot (u^{(I)}(x) - U^{(I)}(x)) \, dV, \quad (1)$$

where the second-order tensor $\chi^{(I)}$ simply takes diagonal matrix form, i.e., $(\chi^{(I)}(x))_{ij} = \delta_{ij} \omega_i^{(I)}(x)$ (I=1, 2, ..., M; i, j=1, 2, 3). The weight function $\omega_i^{(I)}(x)$ equals zero if the i-th displacement component is not measured at point x. To include the surface displacement as measurement, $\omega_i^{(I)}(x)$ is considered as a generalized function on the boundary of $\Omega$.

The elastomammography reconstruction follows an iterative optimization procedure as shown in FIG. 1. Although many different iterative optimization methods can be used, a large-scale limited-memory Broyden-Fletcher-Goldfarb-Shanno (L-BFGS) optimization method is used in the following exemplary embodiments. The L-BFGS method requires user-supplied gradients of the objective function, i.e., $\partial \Phi / \partial \lambda$ and $\partial \Phi / \partial \mu$. Conventional continuum formulas for the gradients have been derived by Oberai et. al. ("Solution of inverse problems in elasticity imaging using the adjoint method," *Inverse Problems*, 19, 297-313. 2003; hereby incorporated by reference in its entirety) for isotropic elastography, and Liu et al. ("Tomography-based 3-D anisotropic elastography using boundary measurements," *IEEE Trans. Med. Imaging*, vol. 24, no. 10, pp. 1323-1333, 2005; hereby incorporated by reference in its entirety; herein after "Liu et al. (2005)) for general anisotropic cases. Finite-element presentations for the objective function $\Phi$ and its gradients can be obtained from the continuum formulas.

Following conventional standard finite element procedures (see, e.g., T. Belytschko et al., *Nonlinear Finite Elements for Continua and Structures*, New York: John Wiley & Sons, LTD, 2000; hereby incorporated by reference in its entirety), the displacement field $u^{(I)}(x)$ can be discretized as vector $u^{(I)}$ which satisfies the equilibrium equation $$Ku^{(I)}=F^{(I)} \ (I=1,2,\ldots,M), \quad (2)$$

where the vector $F^{(I)}$ represents the nodal force. Once a finite-element mesh is generated and a discretization method is selected, the stiffness matrix K depends only on the Lamé parameters $(\lambda(x), \mu(x))$. The measured displacement field $U^{(I)}(x)$ can also be discretized as vector $U^{(I)}$. Therefore, the objective function (Eq. (1)) reads $$\Phi(\lambda(x), \mu(x)) = \sum_{I=1}^{M} (u^{(I)} - U^{(I)})^T X^{(I)} (u^{(I)} - U^{(I)}), \quad (3)$$

in which the matrix $X^{(I)}$ corresponds to the weight function $\chi^{(I)}(x)$, and has the same dimension as the stiffness matrix K.

The gradients of $\Phi$ can be calculated using $$\delta\Phi = \sum_{I=1}^{M} (u^{(I)})^T \delta K \ w^{(I)}, \quad (4)$$

where the adjoint displacement $w^{(I)}$ is the solution of $$Kw^{(I)}=-2X^{(I)}(u^{(I)}-U^{(I)}) \ (I=1,2,\ldots,M) \quad (5)$$

It is noted that $u^{(I)}$ and $w^{(I)}$ share the same Cholesky factorization for the stiffness matrix K, thus the computational expense for solving $w^{(I)}$ (Eq. (5)) is minimal once $u^{(I)}$ is solved using Eq. (2).

In the elastomammography method in accordance with an embodiment of the invention, anatomic structures of the normal breast tissue and tumor are prescanned. Therefore, the breast can be modeled as a piecewise homogenous medium, with uniform Lamé parameters $(\lambda_{tissue}, \mu_{tissue})$ for the normal breast tissue region, and uniform parameters $(\lambda_{tumor}, \mu_{tumor})$ for the tumor region. Consequently, there are four gradients to be calculated:

$$\frac{\partial \Phi}{\partial \lambda} = \sum_{I=1}^{M} \sum_{N} (u_e^{(I)})_N^T \frac{\partial (K_e)_N}{\partial \lambda} (w_e^{(I)})_N, \quad (6)$$

$$\frac{\partial \Phi}{\partial \mu} = \sum_{I=1}^{M} \sum_{N} (u_e^{(I)})_N^T \frac{\partial (K_e)_N}{\partial \mu} (w_e^{(I)})_N,$$

in which the inner summations are taken over all the elements in the tissue region for the gradients $\partial\Phi/\partial\lambda_{tissue}$ and $\partial\Phi/\partial\mu_{tissue}$, and over all the elements in the tumor region for the gradients $\partial\Phi/\partial\lambda_{tumor}$ and $\partial\Phi/\partial\mu_{tumor}$. In Eq. (6), $(K_e)_N$ is the element stiffness matrix of the N-th element, and $(U_e^{(I)})_N$ and $(w_e^{(I)})_N$ are the element nodal displacements with the I-th loading. It is also noted that $\partial(K_e)_N/\partial\lambda$ and $\lambda(K_e)_N/\partial\mu$ are constant matrices for the N-th element. Further, it is noted that more tissue regions having different parameters may be included in the above calculations.

Simulations are performed with numerical breast phantoms to demonstrate the effectiveness of the elastomammography method. Two 3-D breast phantoms are used for the study, each containing one and two tumors, respectively. To simulate mammography compression, two types of loadings are applied, respectively, on the phantoms from different loading angles. Surface forces and part of the boundary displacements are extracted from the forward computation results, in compliance with the capability of projective imaging, and are used as input for the reconstruction. In the following text, unit is "cm" for length and displacements, "kPa" for elastic moduli, and "kN" for nodal forces.

Figure 2A:
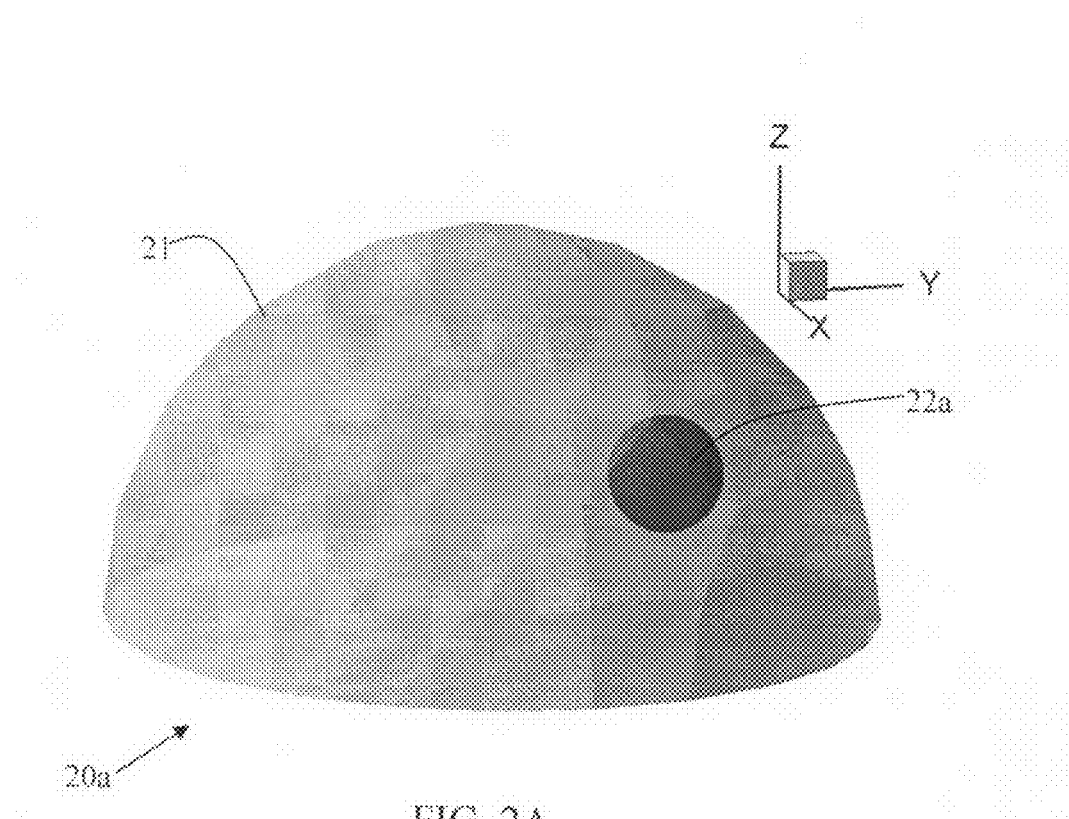
FIGS. 2A and 2B show breast phantoms with one and two tumors, respectively.

In an exemplary study, phantom 20a, which has a half-spherical matrix 21 and an embedded spherical inclusion 22a, is used and is illustrated in FIG. 2A. The matrix 21, which is 10 cm in diameter and is centered at (x, y, z)=(0, 0, 0), simulates normal breast tissues. The inclusion 22a, which is 1.5 cm in diameter and is center at (2, 1.75, 2.25), simulates a tumor.

Figure 2B:
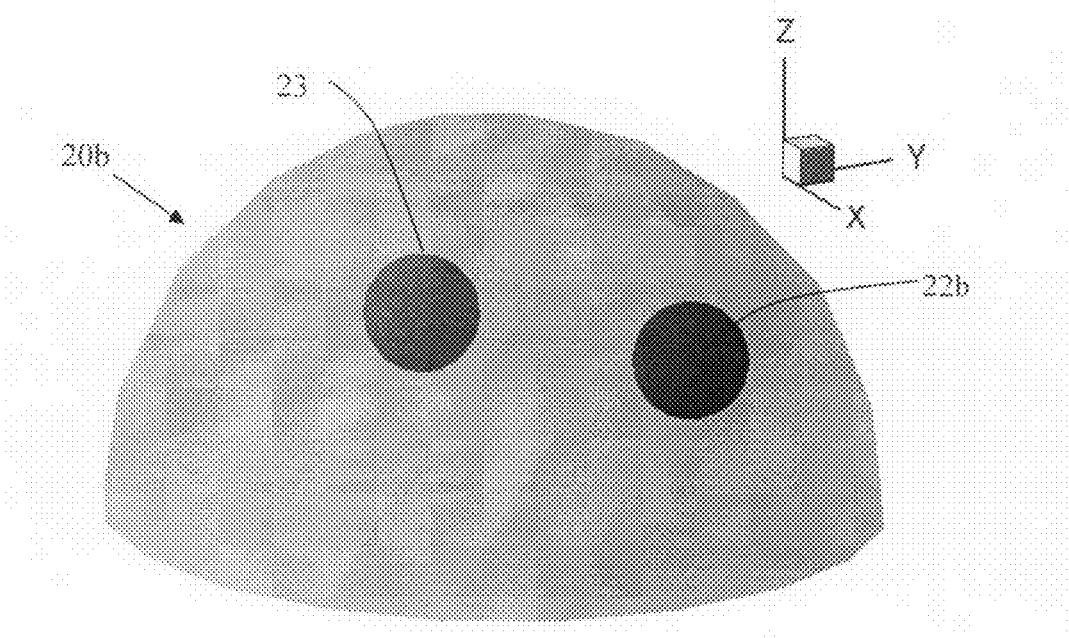

Phantom 20b, shown in FIG. 2B, is similar to the phantom 20a, but has one more tumor 23 at (−1.8, 0, 2), which has the same size as the tumor 22b. The phantoms are discretized with standard 3-D tetrahedral elements. For example, discretized phantom 20a consists of 1114 nodes and 6070 elements, and discretized phantom 20b consists of 1657 nodes and 9340 elements.

The materials are assumed isotropic. The Lamé parameters $(\lambda, \mu)$ are (25, 7.5) for the soft breast tissue and are (125, 25) for the tumor, as designed in both the phantoms. The Young's modulus E and the Poisson ratio v are related to Lamé parameters via $$E = \frac{\mu(3\lambda + 2\mu)}{\lambda + \mu}, \ v = \frac{\lambda}{2(\lambda + \mu)}, \ \lambda = \frac{Ev}{(1+v)(1-2v)}, \ \mu = \frac{E}{2(1+v)}. \quad (7)$$

Hence, (E, v) are (20.769, 0.38462) for soft tissue and (70.833, 0.41667) for tumor. Note that the tumor is assumed approximately 3.5 times as stiff as the surrounding tissue. In general, a tumor is much stiffer than the surrounding normal tissues. However, the ratio between the stiffness of cancerous and normal breast tissues found in the literature shows variations from a few times to tens times (P. Wellman et al., "Breast tissue stiffness in compression is correlated to histological diagnosis," *Harvard BioRobotics Laboratory Technical Report*, 1999). Skovoroda et al. ("Quantitative analysis of the mechanical characteristics of pathologically altered soft biological tissues," *Biofizika*, 40, 1335-1340, 1995) recognized that this is partially due to the nonlinearity effect in which the apparent stiffness increases with the strain applied. Effects of the contrast ratio on elastomammography will be discussed later.

Figure 3A:
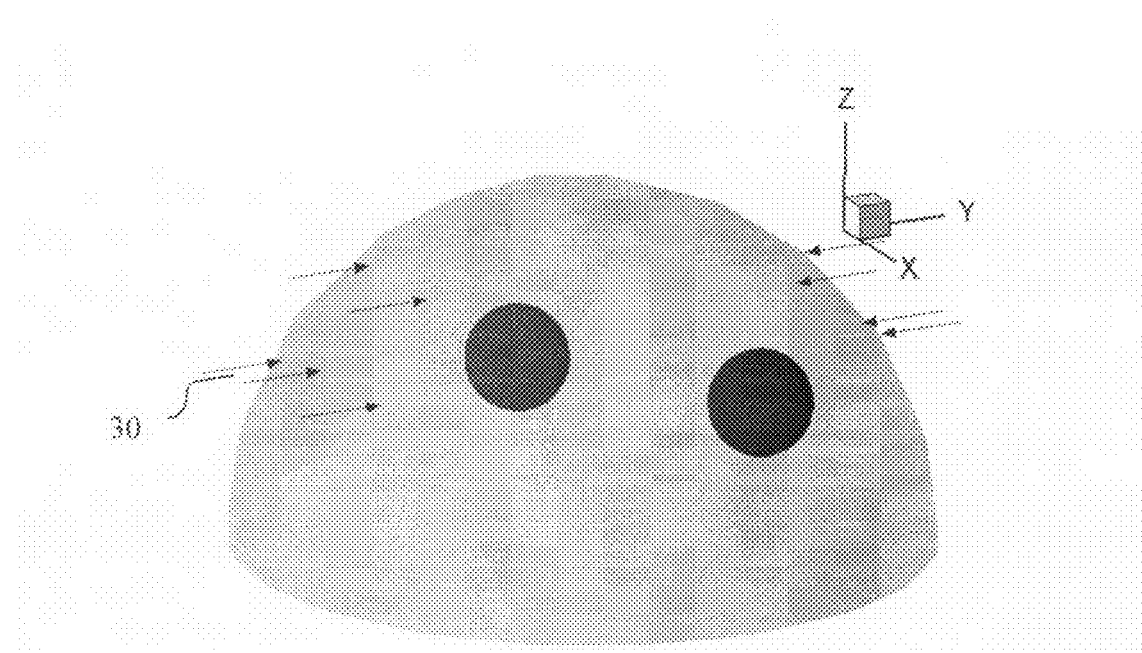
FIGS. 3A and 3B illustrate a compression nodal force applied to a phantom in a 3-D view and a top view, respectively.
Figure 3B:
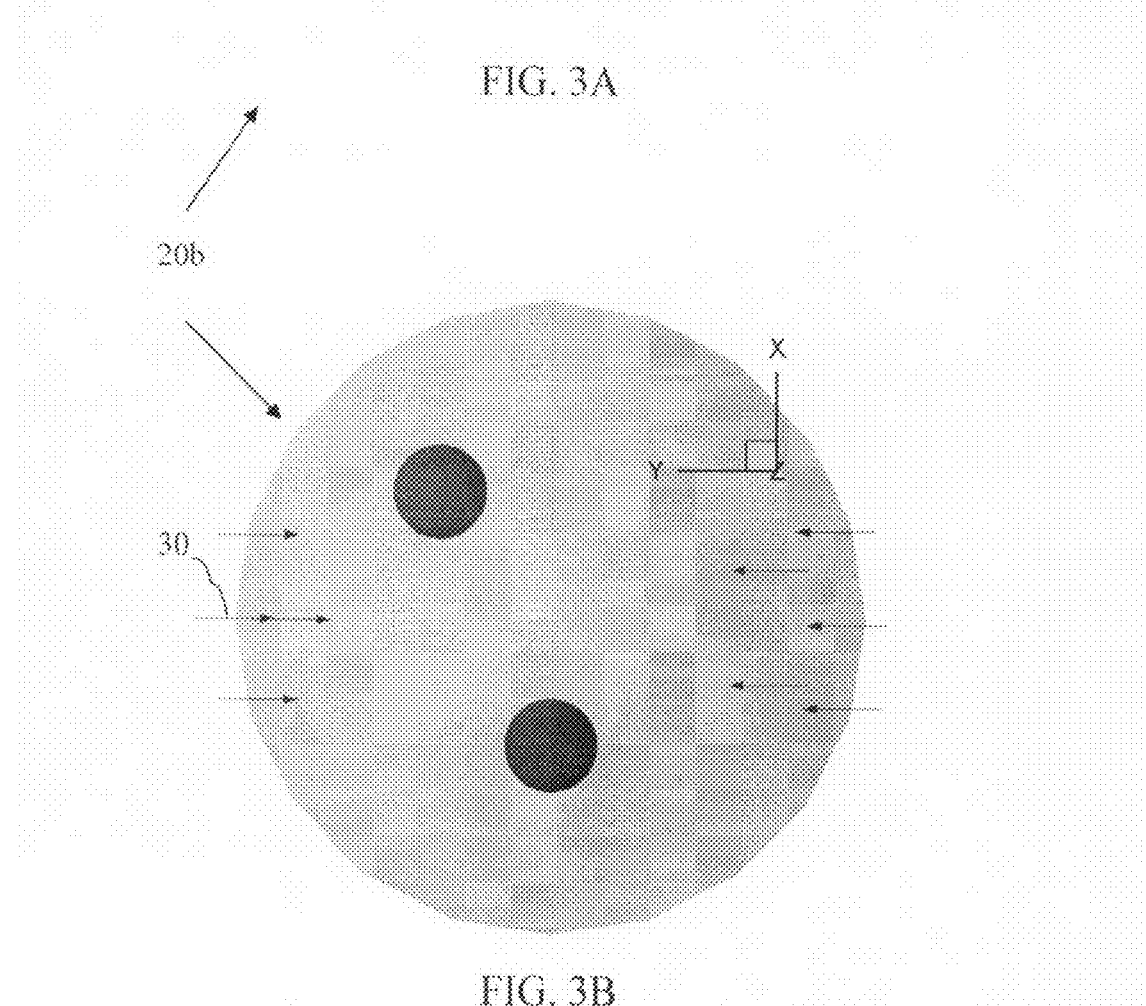
Figure 4A:
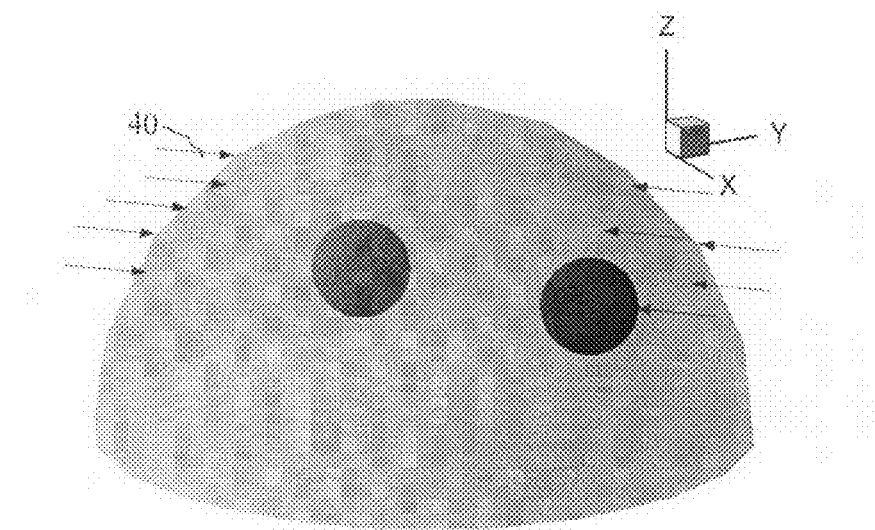
FIGS. 4A and 4B illustrate another compression nodal force applied to a phantom in a 3-D view and a top view, respectively.
Figure 4B:
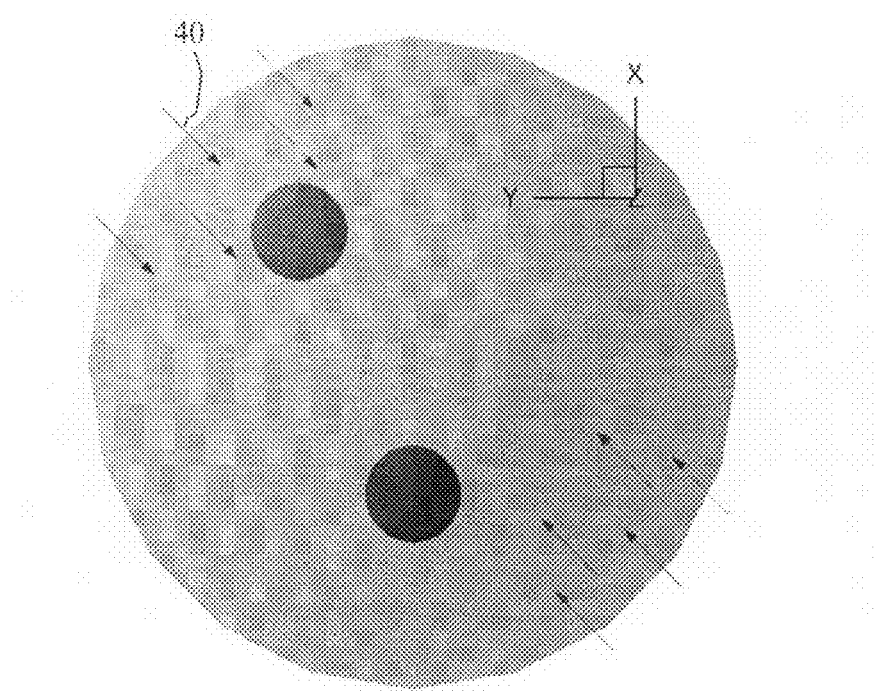

In the simulations, the displacements are zero on the base surface, i.e., where z=0. Two compression loadings are applied on the upper surface of breast phantoms 20a and 20b. For the first loading, a nodal force of 0.005 kN in the Y direction, shown as arrows 30 in FIGS. 3A (3-D view) and 3B (top view), is applied on some of the surface nodes of phantom 20a. The second loading applies a nodal force 40 having components $|F_x|=|F_y|=0.004$ kN on another set of surface nodes, as shown in FIGS. 4A (3-D view) and 4B (top view). The loading directions 30 and 40 are shown to have a difference of $\pi/4$, which is a clinically-preferred angle because of tissue directions. However, other sets of nodal forces with different directions can be used. For convenience, we denote the direction with the first loading as "direction 1", and that with second loading as "direction 2".

Figure 5A:
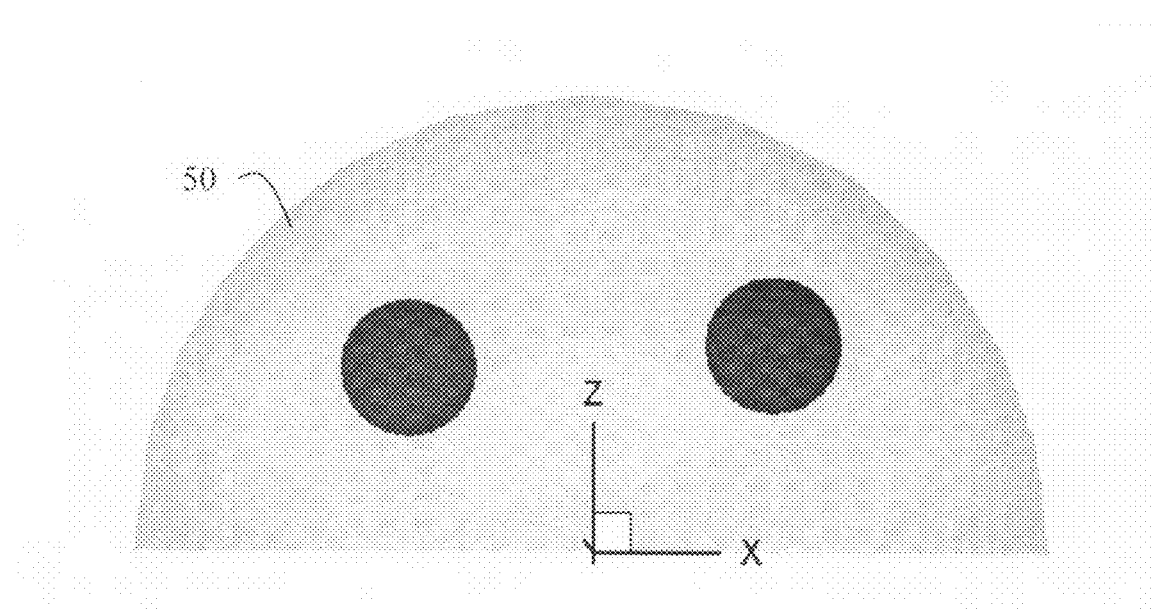
FIGS. 5A and 5B show the undeformed projection and the deformed projection, respectively.
Figure 6A:
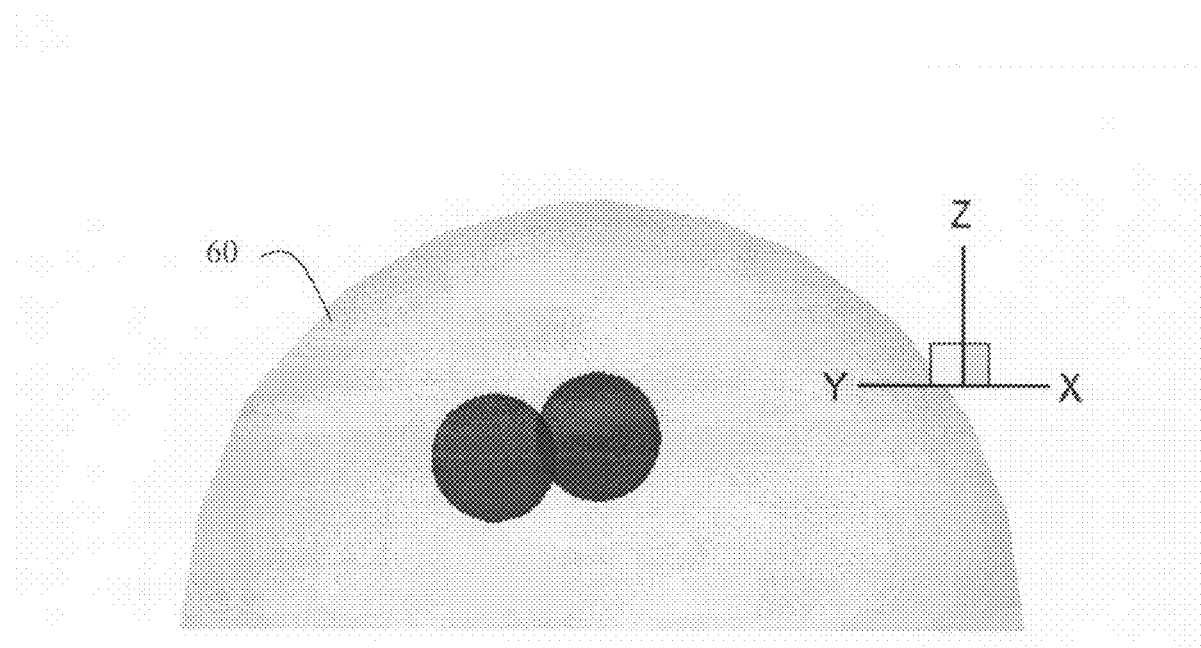
FIGS. 6A and 6B show the undeformed projection and the deformed projection for another loading.

Given the Lamé parameters for normal breast tissue and tumor(s), the deformations in response to the external first and second loadings are respectively obtained by solving finite element equation (2). First, the external surface of a breast at an undeformed state is reconstructed from images taken with a 3-D camera. Next, for each external loading, two mammography projections are made in the compression direction; i.e., one projection with undeformed state, and one with deformed configuration. The shape and location of the tumor(s) can further be estimated from the undeformed projections along different orientations. It is recognized that real tumors may be irregular in shape and be difficult to reconstruct accurately with limited number of projections. As a first order approximation, tumors may be assumed to be spherical, and to deform into ellipsoids. The initial size and center of the tumors are readily estimated with two undeformed projections made in different directions, e.g., directions 1 and 2 in the present simulations, as plotted with FIG. 5A (viewed from direction 1) and FIG. 6A (viewed from direction 2) for phantom 20b. Note that phantom 20a is considered as phantom 20b with absence of the tumor initially at (−1.8, 0, 2).

Figure 5B:
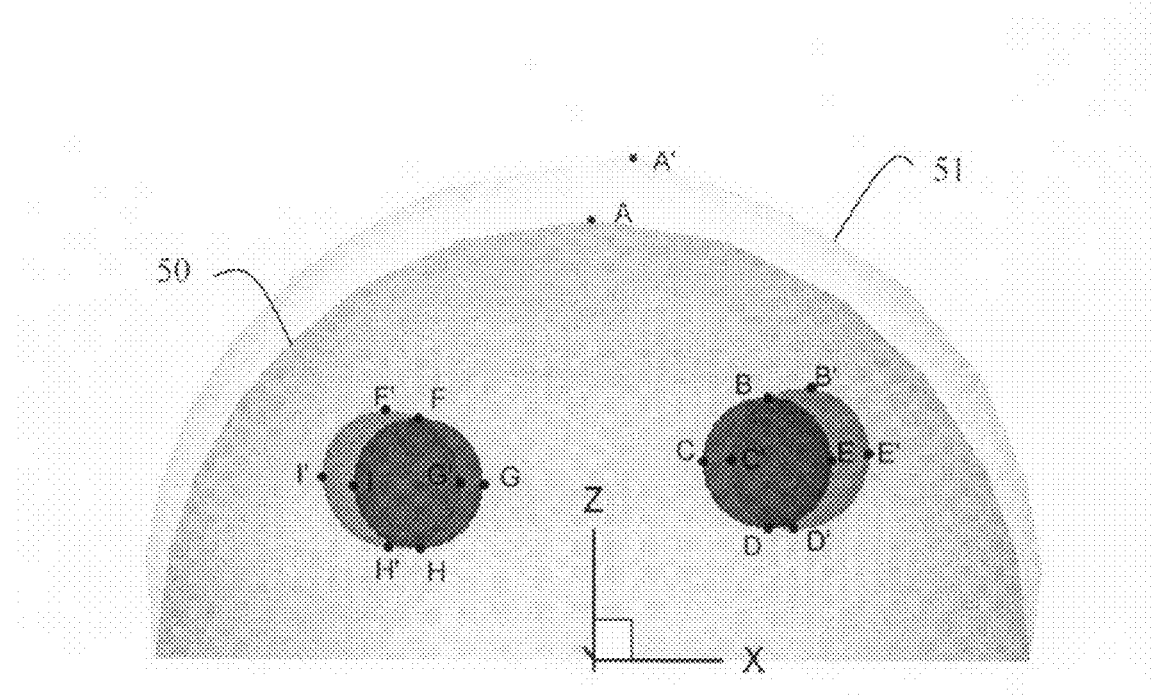

Displacement information from projection of deformed configurations is extracted. Based on the micromechanics theory for deformation of an inclusion in a large medium (e.g., J. D. Eshelby, "The determination of the elastic field of an ellipsoidal inclusion, and related problems," *Proc. Royal Soc. London, A*241, 376-396, 1957), it may be estimated that an initially spherical tumor deforms into an ellipsoid. Because of the relatively simple uniaxial compression loadings applied in mammography, it may be further approximated that vertexes of an object in an undeformed projection remain vertexes in the corresponding projection after compression deformation. For example, in FIG. 5B for the first loading, point A is the top vertex of tissue in the undeformed projection 50. It moves to vertex A' in the deformed projection 51.

Figure 6B:
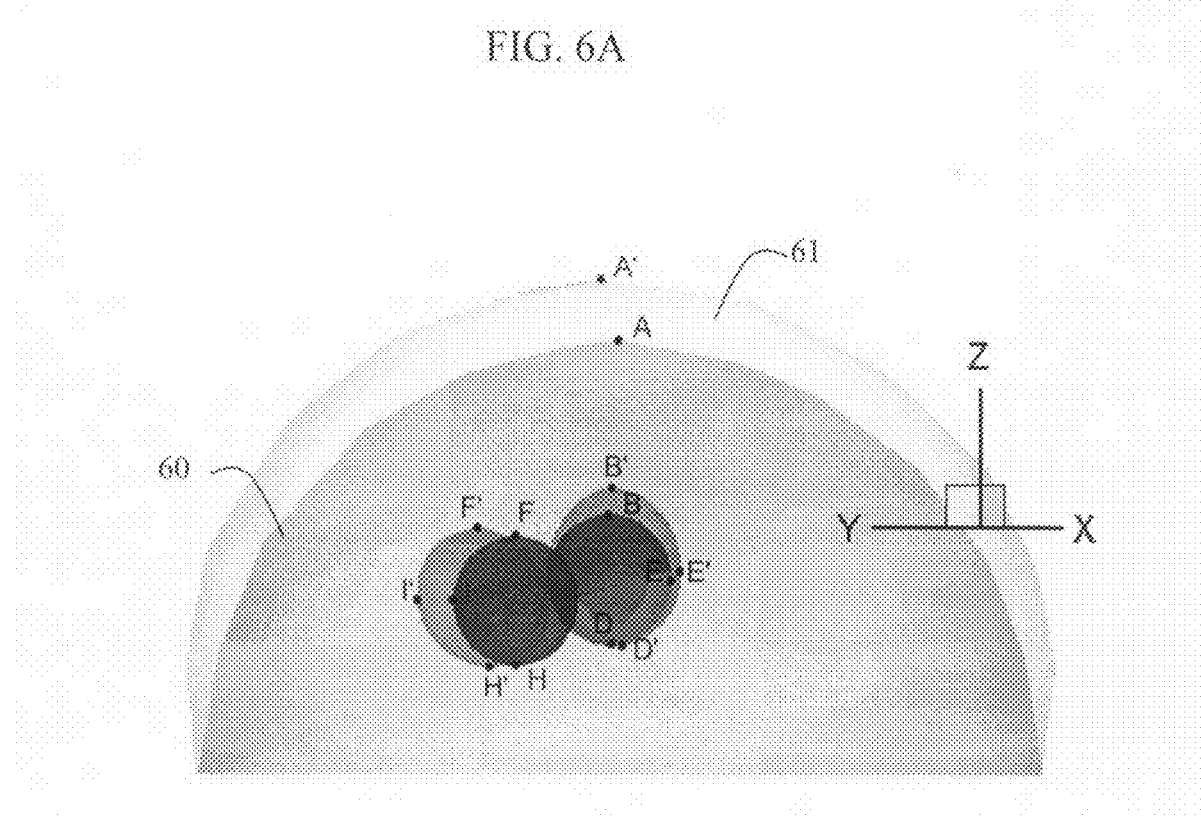

Points B~I are vertexes of the tumors in the undeformed projection 50. They displace to vertexes B'~I', respectively. Thus, by measuring the vertex locations in projections before and after a deformation, their displacement information can be obtained. For example, displacement components $u_x$ and $u_z$ in the first loading for vertexes A~I can be extracted from the projections as in FIGS. 5A and 5B. Displacement information resulting from the second loading can be obtained from projections in FIGS. 6A and 6B, wherein the undeformed projection 60 and the deformed projection 61 are shown.

It is noted that the two tumors partly overlap in the projections in direction 2, and vertexes C and G are in shadow. For such a case, the vertex displacements are still attainable according to the grey density information in the projections, although some accuracy may be lost. The collected displacement data are denoted as $U^{(1)}$ and $U^{(2)}$ for elastomammography reconstruction.

Accurate displacement measurement with high spatial resolution will benefit elastography reconstruction in general. However, pinpoint tracking of large number of material points in an object is still a challenge in medical imaging, in particular for simple mammography projections that lack natural landmarks. Therefore, in accordance with an embodiment of the invention, only displacements of a few special points extracted directly from projections are used. As described above, the points include top vertex on the upper breast surface (A in FIG. 5B) and vertexes of the tumors in projections (B~I). Displacements measured at other points using a 3-D camera, for example, on the external surface, will enhance the efficiency and accuracy of elastomammography.

With the described data acquisition method, displacements at some key points are extracted from deformed and undeformed projections with two compression loadings, and are used as measured $U^{(1)}$ and $U^{(2)}$ for elastomammography reconstruction. Compression nodal forces applied on the surface are also known with the loadings. Given initial estimate, the Lamé parameters for tissue and tumor are reconstructed following the optimization procedure shown in FIG. 1.

An ideal case is considered first. For example, the displacements, geometry, and compression nodal forces are exactly measured, and are used as input for reconstruction. Reconstructions results are shown in Table 1, where rows "Ideal I" and "Ideal II" are for phantom 20a and phantom 20b, respectively.

Figure 7A:
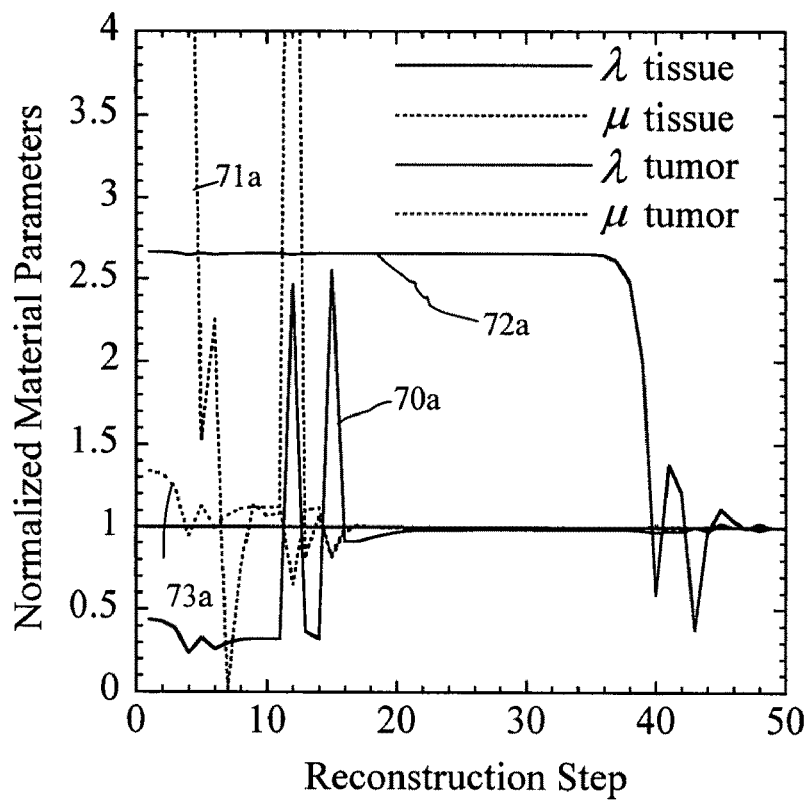
FIGS. 7A and 7B show the convergent loci of elastomammography reconstruction for the two phantoms.
Figure 7B:
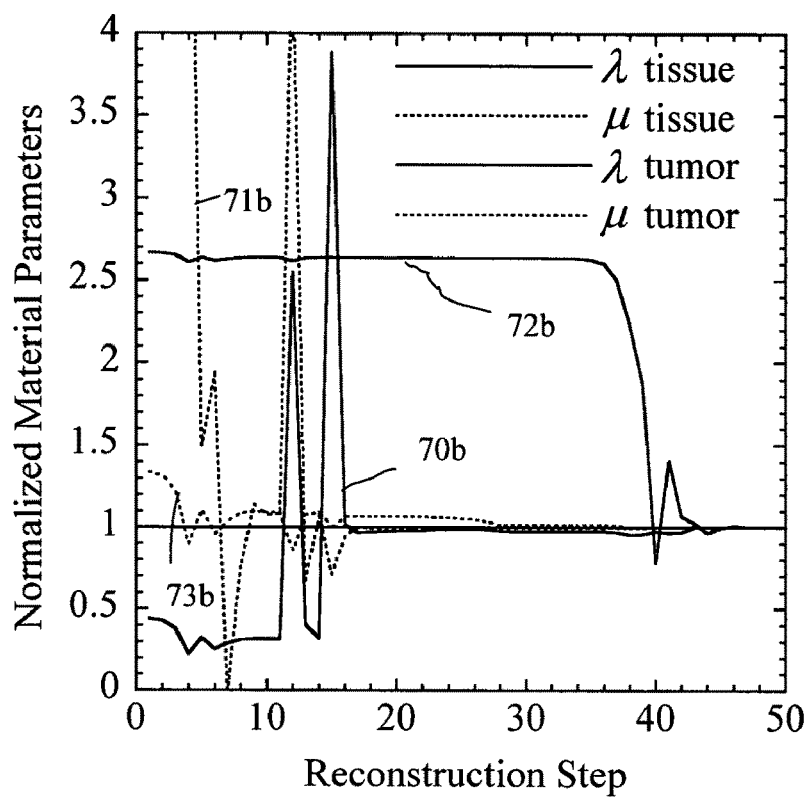

Convergent loci of the Lamé parameters ($\lambda$, $\mu$) are plotted with FIGS. 7A and 7B. The loci for phantom 20a (shown in FIG. 7A) and phantom 20b (shown in FIG. 7B) are very similar. It is observed that ($\lambda$, $\mu$) of the tissue (curves 70a and 71a for phantom 20a in FIG. 7A; curves 70b and 71b for phantom 20b in FIG. 7B) approach their respective real values rapidly. Some peaks are seen between step 10 and 20, and are probably due to numerical noises. However, the curves converge quickly. After about 20 iteration steps, their respective relative errors are well within a range of 5%. Only some minor adjustments are seen after step 20.

In contrast, Lamé parameters of the tumor converge slower, as shown in FIG. 7A for phantom 20a (curve 72a for $\lambda$; curve 73a for $\mu$) and FIG. 7B for phantom 20b (curve 72b for $\lambda$; curve 73b for $\mu$). In particular, the values of $\lambda$ (72a for phantom 20a; 72b for phantom 20b) start to converge to the real values after about 40 steps.

After about 50 steps, all parameters are accurately identified, with the largest error of about ±0.18% (for $\lambda$ of tumor). Reconstructions using different initial estimates have been conducted. Very similar convergent profiles are found for the parameters, and highly accurate results are obtained. These results demonstrate the efficiency and uniqueness of the elastomammography using projective measurements.

TABLE 1

Initial Estimate and Reconstructed Results for Elastomammography

| | Tissue | | | | Tumor | | | |
|---|---|---|---|---|---|---|---|---|
| | $\lambda$ | $\mu$ | E | $\nu$ | $\lambda$ | $\mu$ | E | $\nu$ |
| Real | 25 | 7.5 | 20.769 | 0.38462 | 125 | 25 | 70.833 | 0.41667 |
| Estimate | 11 | 194.5 | 399.441 | 0.02676 | 333 | 33.5 | 97.705 | 0.45430 |

TABLE 1-continued

Initial Estimate and Reconstructed Results for Elastomammography

| | Tissue | | | | Tumor | | | |
|---|---|---|---|---|---|---|---|---|
| | $\lambda$ | $\mu$ | E | $\nu$ | $\lambda$ | $\mu$ | E | $\nu$ |
| | | | | Reconstruction Results | | | | |
| Ideal I | 24.999 | 7.5 | 20.769 | 0.38462 | 124.817 | 24.999 | 70.815 | 0.41658 |
| Ideal II | 25.012 | 7.5 | 20.764 | 0.38469 | 125.219 | 25.038 | 70.947 | 0.41679 |
| Noise I | 25.155 | 7.495 | 20.764 | 0.38522 | 106.750 | 25.055 | 70.404 | 0.40495 |
| Noise II | 26.048 | 7.503 | 20.82 | 0.38819 | 146.801 | 22.379 | 64.176 | 0.43386 |
| Mismatch I | 24.972 | 7.502 | 20.777 | 0.38449 | 129.398 | 24.901 | 70.929 | 0.41906 |
| Mismatch II | 25.042 | 7.493 | 20.703 | 0.38508 | 155.273 | 26.943 | 78.826 | 0.46283 |

The slower convergent speed of Lamé parameters of the tumor, in particular for $\lambda$, is explained by the roles they play in the deformation due to the applied loadings, as discussed in Liu et al. (2005). In general, parameters with the most significant influence on the deformation are also those that are most accurately and easily identified. The Influence of a parameter depends on size and location of the material region it belongs to, as well as characteristics of the deformation. For the present simulations, $\lambda$ and $\mu$ of the tissue are dominant, while those of tumor(s) are much less influential, due to the small size and deep location of the tumor(s). Slower convergence of $\lambda$ for tumor indicates that the above-described exemplary loadings do not introduce enough volumetric strain in the tumor(s).

The elastomammographic reconstructions described above are conducted using ideal inputs. In practice, several factors will affect the performance of elastomammography. A common concern is noise in displacement measurement. To investigate the capability of the elastomammographic modality and algorithm to handle imperfect real data due to inevitable measurement errors, each component of $U^{(1)}$ and $U^{(2)}$ is added with a randomly selected relative error between −5% and 5% before being input into the reconstruction procedures.

The results are shown as "Noise I" (for phantom 20a) and "Noise II" (for phantom 20b) in Table 1. The corresponding convergent loci are plotted with FIGS. 8A and 8B. The overall convergent loci are very similar to the "ideal" cases shown in FIGS. 7A and 7B. Lamé parameters ($\lambda$, $\mu$) of the tissue need about 20 steps to approach closely to the real values, while those of the tumor(s) need about 50 steps for convergence. The tissue parameters are very accurately identified, with the largest relative error of 4% for $\lambda$ of phantom 20b, and errors well within ±1% for the others. The Lamé parameters ($\lambda$, $\mu$) of tumor(s), however, are not as robust, with relative errors of (−14.6%, 0.22%) and (17.4%, −15.5%) for phantom 20a and phantom 20b, respectively.

Figure 8A:
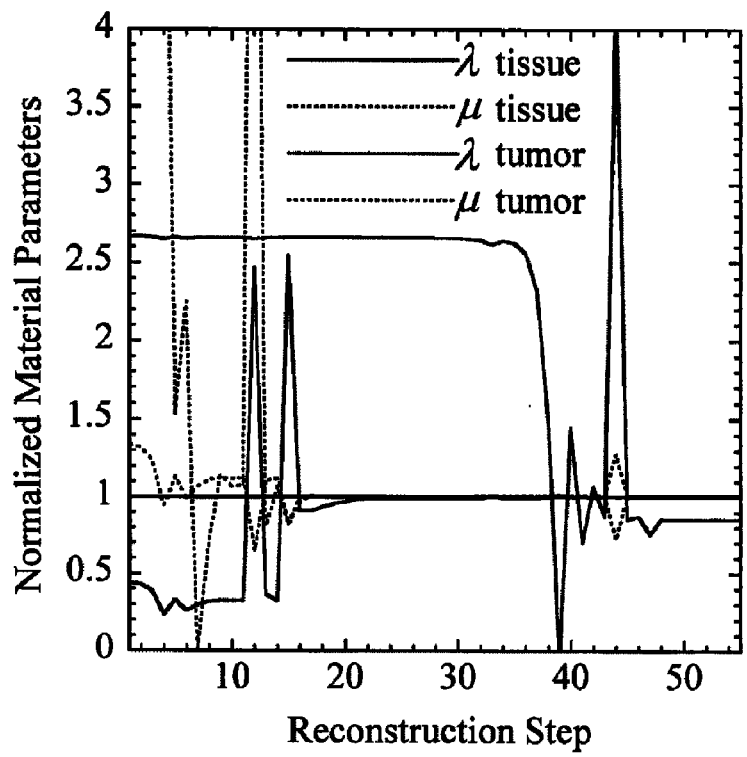
FIGS. 8A and 8B show the convergent loci of elastomammography reconstruction for the two phantoms when noise is present.
Figure 8B:
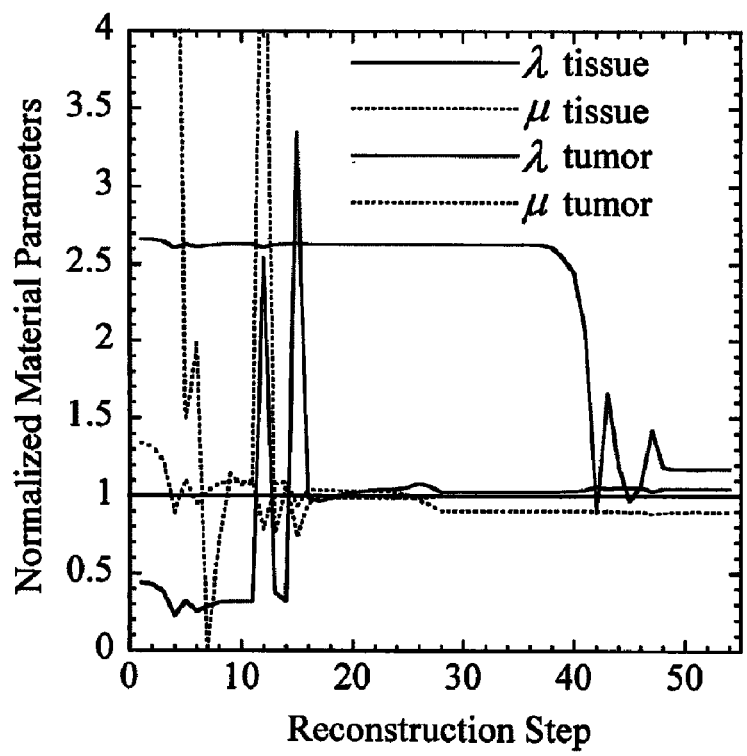

In spite of these reconstruction errors, Table 1 and FIGS. 8A and 8B still positively demonstrate that the elastomammographic results are sufficiently accurate for diagnosis of tumors, noting the significant differences of stiffness between normal tissue, benign and malignant tumors. The better robustness of the tissue parameters is also explained by the strong roles they play in the deformation. Furthermore, as suggested by Liu et al. (2005), multiple sets of well-designed loadings should help to bring out the influences of all the material parameters, and thus suppress the effects of noise.

Figure 9A:
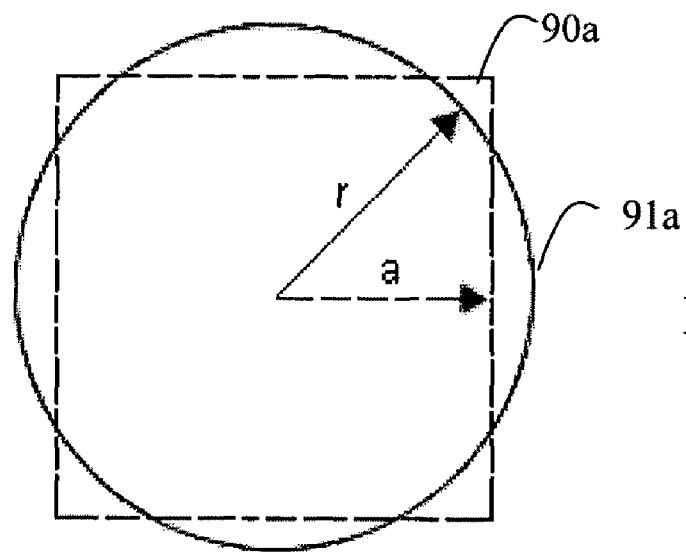
FIGS. 9A and 9B illustrate the geometry mismatch in two different projection directions.
Figure 9B:
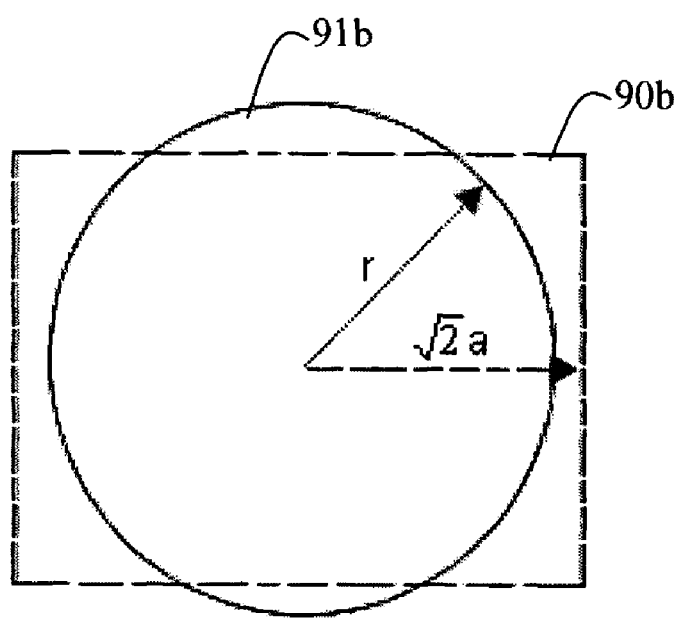

Another concern for elastomammography is providing a geometric depiction of the tumors. The size and location of the tumor are estimated from two undeformed mammography projections. This may introduce a geometric mismatch for practical elastomammography if the tumor is assumed to be a simple sphere. To investigate the effect of a geometric mismatch, the two phantoms were redesigned by replacing the spherical tumors with cubic tumors having an edge length of $3/\sqrt{5}$ cm. Forward simulations were conducted under the same the first loading and the second loading with the new phantoms. Mammography projections were obtained for the new undeformed and deformed configurations. To extract geometric and displacement data from these projections, the spherical approach can still be used. As schematically shown in FIG. 9A, a cubic tumor 90a is approximated with a spherical one 91a. The size and location of the spherical tumor 91a are determined by the two undeformed projections in direction 1 and direction 2. Then, the estimated spherical tumors are used for elastomammographic reconstruction of the material parameters. The results are shown as "Noise I" (for phantom 20a) and "Noise II" (for phantom 20b) in Table 1. Convergent loci are found to be similar to the previous cases, and are not shown.

The tissue parameters again show excellent robustness. The geometric mismatch introduces relative errors less than 0.17%. Due to the relatively small size of the tumor(s), their Lamé parameters ($\lambda$, $\mu$) are more sensitive to geometric mismatch, with relative errors (3.52%, 0.40%) for phantom 20a and (24.2%, 7.78%) for phantom 20b.

In a simplified model where a perfect sphere is assumed to simulate the real tumor, information of deformation can be easily obtained from the projections. However, investigation of geometry mismatch is needed since most of real tumors have irregular shapes. A cube (a rectangle or square in projections) is used to represent a real tumor and a sphere (a circle in projections) approximates it. From FIG. 9A, it can be seen that most of areas between circle and square overlap. The results demonstrate that geometry mismatch does not have a great influence on this reconstruction. It is therefore suggested that, for an irregular shape of a real tumor in projections, a user may choose a circle to approximate it and do reconstruction based on this simplified model.

The material stiffness is a key property that distinguishes benign from malignant tumors. Contrast ratio (CR), defined as the ratio of Young's modulus of tumor and normal breast tissue, can be used to characterize the stiffness property. For benign tumors, contrast ratio typically varies from 2.0 to about 5.0. For malignant tumors, it is considerably higher. Accuracy of elastographic reconstruction depends not only on types of loading and measurement accuracy, but also on the contrast ratio.

To investigate the effect of contrast ratio, elastomammographic reconstructions are constructed using "soft" phantoms and "hard" phantoms, the Lamé parameters ($\lambda$, $\mu$) for which are set to create CR of 1.5 and 8.0, respectively. Table 2 gives the real Lamé parameters and reconstruction results.

Compared to the previous case with CR about 3.5 (Table 1, "Ideal I" and "Ideal II"), results for the soft phantoms (CR=1.5) are even more accurate, in particular for $\lambda$ of the tumor. For the hard phantoms CR=8.0), the tissue parameters are also exact; however, $\lambda$ of tumor carries relative reconstruction errors of about 13% for both phantoms, which is considerably larger than the soft cases with CR=3.5 and 1.5. The reason is that deformation of a relatively softer tumor is larger than a hard one, and thus is more sensitive to small variation of its material parameters. Also as discussed above, $\lambda$ of the tumor seems to have the least influence on the specific deformations considered in the simulations. In general, elastomammography is effective to reveal the contrast ratio, and detect whether a tumor is malignant or benign. A tumor is suspected of malignancy when the contrast ratio is higher than 6. In the present simulations, when the "real" contrast ratio is 8.0, the elastomammographic reconstruction yields 8.11, which is sufficiently accurate for the diagnostic purpose.

TABLE 2

Elastomammographic Simulation Using Phantoms with Different Stiffness CRs

| | Tissue | | | | Tumor | | | |
|---|---|---|---|---|---|---|---|---|
| | $\lambda$ | $\mu$ | E | $\nu$ | $\lambda$ | $\mu$ | E | $\nu$ |
| Contrast Ratio = 1.5 | | | | | | | | |
| Real | 25 | 7.5 | 20.769 | 0.38462 | 54.979 | 10.995 | 31.154 | 0.41667 |
| phantom 20a | 25 | 7.5 | 20.769 | 0.38461 | 54.979 | 10.995 | 31.154 | 0.41667 |
| phantom 20b | 24.928 | 7.5 | 20.766 | 0.38436 | 55.709 | 11.025 | 31.154 | 0.41720 |
| Contrast Ratio = 8.0 | | | | | | | | |
| Real | 25 | 7.5 | 20.769 | 0.38462 | 293.22 | 58.642 | 166.15 | 0.41667 |
| phantom 20a | 24.989 | 7.5 | 20.767 | 0.38458 | 332.56 | 58.676 | 167.23 | 0.42501 |
| phantom 20b | 24.994 | 7.497 | 20.761 | 0.38463 | 331.42 | 59.124 | 168.42 | 0.42431 |

In some cases, displacements measured from a single loading are adequate for unique identification of the Lamé parameters ($\lambda$, $\mu$) of tissue and tumor. However, the measurement may need to include displacement on the entire external surface and the tissue-tumor interface of a breast, requiring more complex imaging equipment. In accordance with an embodiment of the invention, displacement measurement is reduced to a few vertexes, which can be readily obtained from simple mammography projections. A tradeoff is that two or more sets of compression loadings may be needed to obtain adequate identification. The number of sets of compression loadings is determined based on a compromise between more imaging information and restrictions in diagnostic doses.

The above-discussed elastographic reconstruction uses an assumption of linear elasticity theory. However, deformation of most biological soft tissues may be nonlinear. Consideration of nonlinear models is important for elastography in clinical applications.

A continuum description is used for the breast tissues. Assuming a biological object represented by $\Omega^0$, a displacement tensor at Lagrangian coordinates X within the object $\Omega^0$ may be represented with u(X). A deformation gradient can be expressed as $F = I + \partial u/\partial X$, and the Green strain is $E = (F^T \cdot F - I)/2$ (where "·" denotes contraction operation between two tensors).

The breast tissues are assumed hyperelastic, e.g., the second Piola-Kirchhoff stress is $S = \partial W(E; p)/\partial E$, where W is strain energy and p denotes material parameters in the model. In the linear cases discussed earlier, $p=(\lambda, \mu)$. In the nonlinear cases discussed below, p may include more parameters, e.g., $p=(\lambda, \mu, \gamma)$. It is noted that even more parameters may be included in p for a more accurate description of the material properties.

The symbol ";" is used to separate material parameters from deformation variables. The governing equation and boundary conditions for u are $$\begin{cases} \nabla \cdot (S \cdot F^T) + b(X, u(X)) = 0 & X \in \Omega^0 \\ N(X) \cdot (S \cdot F^T) = t(X, u(X)) & X \in \Gamma_t^0 \\ u(X) = \bar{u}(X) & X \in \Gamma_u^0 \end{cases} \quad (8)$$

The boundary of $\Omega^0$ consists of $\Gamma_t^0$, with N being the outer normal, on which external force t is applied, and $\Gamma_u^0$ being where displacement $\bar{u}$ is prescribed.

In general, both the body force b and the surface force t are deformation dependent. Using finite-element method, the displacement u is discretized as nodal displacement vector $\{U\}=\{u_1, u_2\}^T$, where $u_2$ corresponds to $\bar{u}$ prescribed on $\Gamma_u^0$, and $u_1$ is to be solved from nonlinear equations:

$$\begin{Bmatrix} f_1^{in}(u_1, u_2; p) \\ f_2^{in}(u_1, u_2; p) \end{Bmatrix} - \begin{Bmatrix} f_1^{out}(u_1, u_2) \\ f_2^{out} \end{Bmatrix} = \begin{Bmatrix} 0 \\ 0 \end{Bmatrix}. \quad (9)$$

The internal nodal force $f^{in}$ corresponds to stress S, i.e., it depends on $u_1$ and material parameters p. The external nodal force $f_1^{out}$ corresponds to the prescribed surface force t on $\Gamma_T^0$ and body force b in $\Omega^0$, and $f_2^{out}$ is the unknown constraint force on $\Gamma_u^0$. A classic quasi-Newton method is employed to solve (2) for $u_1$.

Experimental measurements for elastography include displacement and force as discussed earlier with respect to the linear models. The same finite-element method can also be used to discretize the biological object $\Omega^0$ in the nonlinear models. Subsequently, the measurements are discretized into nodal displacements and nodal forces.

The measurements may have the following different situations: (i) If displacement at a node along a direction is known (prescribed or measured after deformation), it will be included into $u_2$ that is considered "prescribed" in equations (9). The corresponding nodal force (known or unknown) will be in the constraint force, denoted as $F_2^M$. Note that $F_2^M$ corresponds to $f_2^{out}$ in equation (9). (ii) All the other nodal displacements will be in $u_1$, and the corresponding nodal force will be in $f_1^{out}$. It is noted that in this situation $f_1^{out}$ must be considered "prescribed", to fulfill the requirement of the well-postness of a solid mechanics problem.

For an elastography problem, the obtained $u_2$ and $f_1^{out}$ are known in equation (9), and the constraint force $F_2^M$ is considered as "measurement". For given material parameters p, the unknown displacement $u_1$ and constrain force $f_2^{out}$ (which depends on p) will be solved from equation (9). The algorithm in accordance with an embodiment of the invention thus searches for p such that the overall difference between measured $F_2 M$ and computed $f_2^{out}$ is minimum, that is $$\min_p \Phi(p) = (F_2^M - f_2^{out})^T X (F_2^M - f_2^{out}), \quad (10)$$

where the weight matrix X is diagonal, i.e., $X=\text{diag}(\alpha_1, \alpha_2, \ldots, \alpha_j, \ldots)$, where $\alpha_j=1$ when the j-th component of $F_2 M$ is measured, and $\alpha_j=0$ otherwise. The present algorithm is mathematically equivalent to the cases discussed earlier with respect to the linear model, where displacement is used as "measurement". For breast tissue whose tangent stiffness significantly increases with strain, this "force version" shows better numerical efficiency.

Efficient and robust optimization-based elastography schemes require user-supplied gradient $\partial \Phi / \partial p$. Previous elastographic studies used approximate finite-difference method or direct method for the gradient. The computational expense of these methods increases proportionally with the number of material parameters, and becomes unaffordable for problems involving finite strain deformation. In accordance with an embodiment of the invention, an adjoint method is used to compute the gradient analytically as described in Liu et al. (2005).

Finite element formulas of the present "force version" is derived. After $u_1$ is solved for given p, the gradient is readily obtained as:

$$\frac{\partial \Phi}{\partial p} = \begin{Bmatrix} w_1 \\ w_2 \end{Bmatrix}^T \begin{Bmatrix} \partial f_1^{in}/\partial p \\ \partial f_2^{in}/\partial p \end{Bmatrix} \quad (11)$$

where the virtual adjoint displacements $w_1$ and $w_2$ are solved from linear equations $$\begin{cases} w_2 = 2X(F_2^M - f_2^{out}) \\ (K_{11}^{eff})^T w_1 = \left(\frac{\partial f_2^{in}}{\partial u_1}\right)^T w_2 \end{cases} \quad (12)$$

in which $K_{11}^{eff}$ is the tangent stiffness matrix. The most significant features of the adjoint method are its analytical formulation, high accuracy, and computational efficiency. Because $K_{11}^{eff}$ and its factorization (LU) have been calculated when solving equation (9), the additional expense for $w_1$ and $w_2$ is minimal. Furthermore, it needs to solve only one linear equation (11) regardless of the number of unknown parameters in p.

Figure 10:
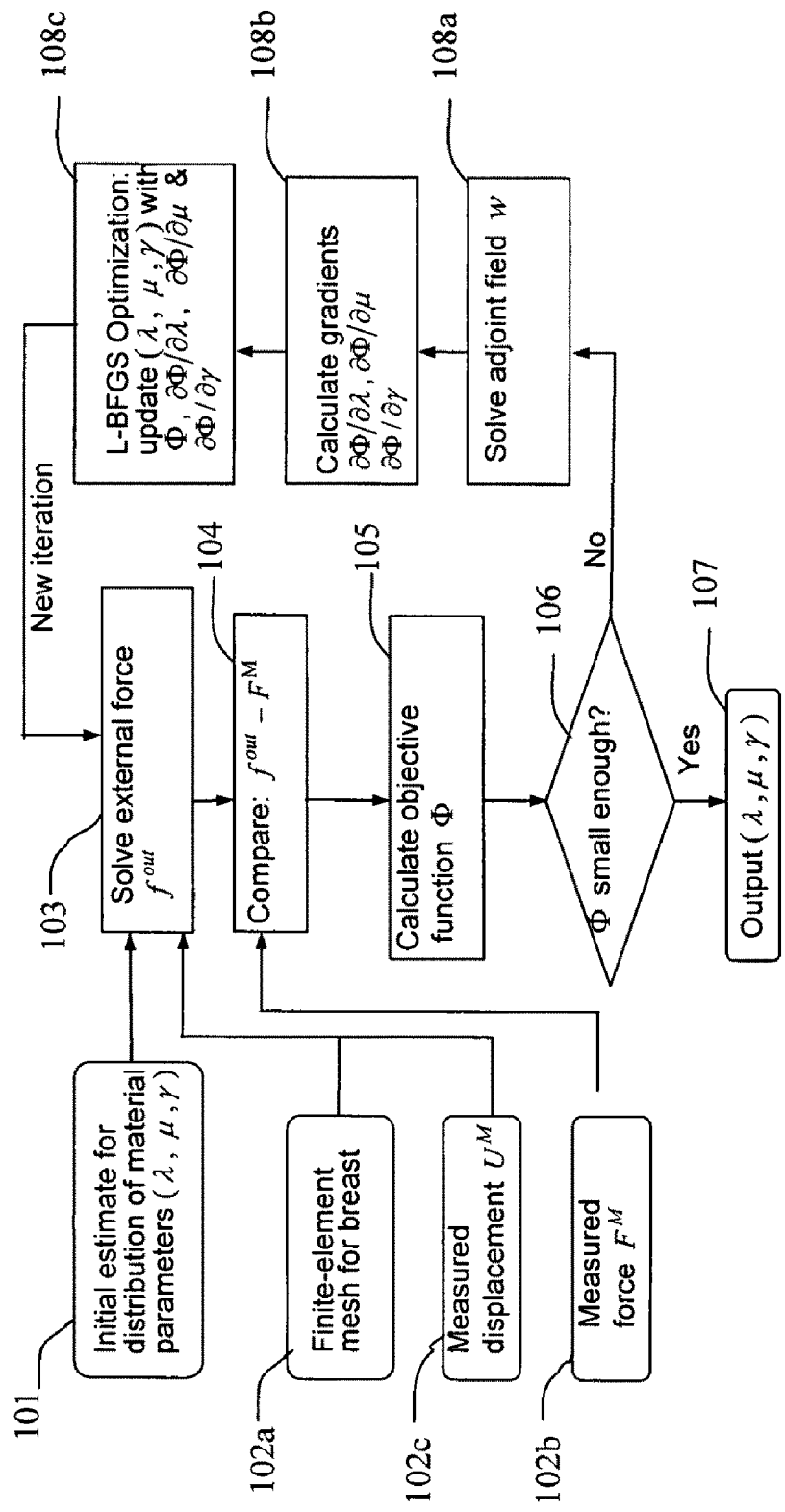
FIG. 10 is a flowchart illustrating a non-linear elastomammography method in accordance with an embodiment of the invention.

As shown in FIG. 10, an L-BFGS subroutine is used for the optimization-based nonlinear elastography. In step 101, an initial estimate for Lamé parameters $\lambda$, $\mu$, and $\gamma$ is obtained. A finite-element mesh for breast is built in step 102a. A force $F^M$ is measured in step 102b, and a displacement $U^M$ in response to the force $F^{(I)}$ is measured in step 102c. Results from steps 101, 102a and 102c are input to equations (11), to solve the external force $f^{out}$ in step 103. In step 104, the calculated external force foul from step 103 is compared with the measured force $F^M$ from step 102b. In step 105, the objective function $\Phi$ is calculated. The objective function $\Phi$ is evaluated in step 106. If $\Phi$ is smaller than a predetermined threshold, the parameters ($\lambda$, $\mu$, $\gamma$) are output in step 107 and are further used for diagnostics purposes. If the objective function $\Phi$ is not satisfactorily small, adjoint displacement field $w^{(I)}$ are solved in step 108a. In step 108b, the gradients of the objective function $\Phi$ are calculated, and input ($\lambda$, $\mu$, $\gamma$) values are updated in step 108c. Steps 103-106 are repeated using the updated ($\lambda$, $\mu$, $\gamma$) values.

Phantom simulations are used to identify the nonlinear elastic properties of the fatty, glandular and cancerous tissues in a breast. A 3-D heterogeneous breast phantom using data extracted from real CT images is built for this purpose. A model developed by Fung (Fung, Y. C., *Biomechanics-mechanical properties of living tissues*, Springer, 1993; hereby incorporated by reference in its entirety) is applied to the phantom to describe the tissue deformation. Loadings are applied and forward problem computations are conducted. Boundary forces are extracted from the forward computation results, and are used as input for reconstruction for the breast phantom.

Figure 11:
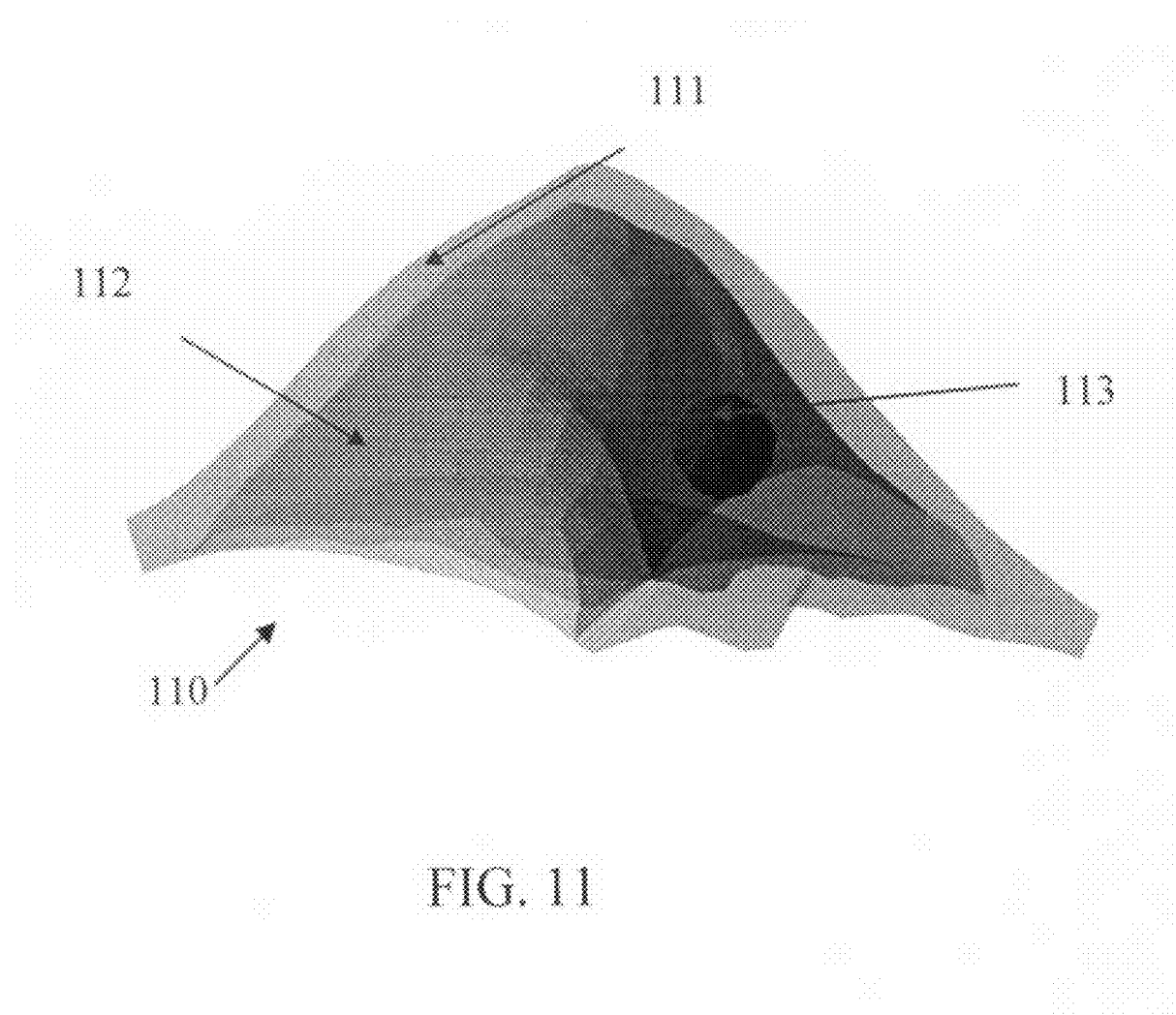
FIG. 11 illustrates a 3-D heterogeneous breast phantom extracted from real CT images.
Figure 12:
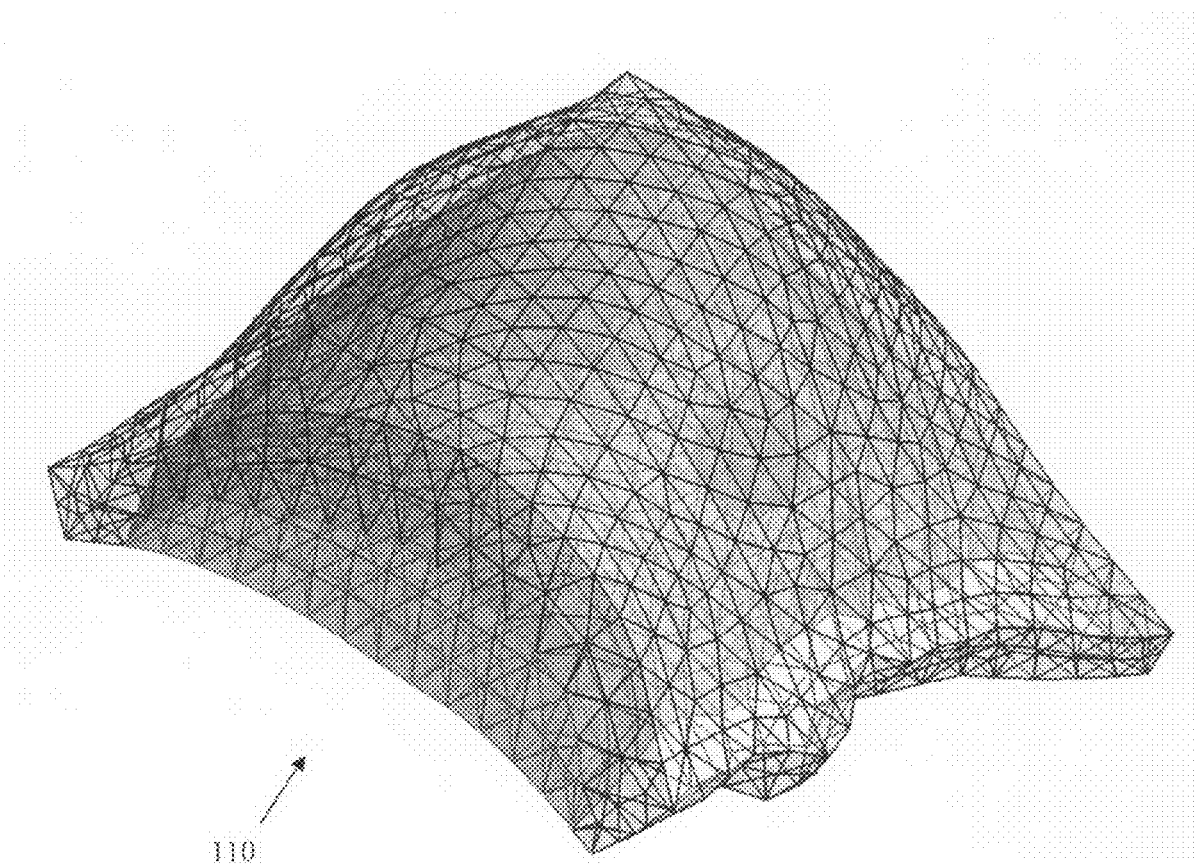
FIG. 12 illustrates a finite-element discretization of the breast phantom.

A phantom 110 containing fatty tissue 111, glandular tissue 112, and a tumor 113 is established and is illustrated in FIG. 11. Boundaries of these regions are described using sets of splines. The phantom is discretized with standard 3D tetrahedral elements, consisting of 7303 elements and 1583 nodes, as shown in FIG. 12.

Hyperelastic models are used to represent the stress-strain relation of biological soft tissue, and the stress-strain relation can be represented by the strain-energy function $$S = \partial W(E;p)/\partial E, \quad (13)$$

where S is the second Piola-Kirchhoff stress, E is Green strain, W is strain energy and p denotes material parameters in the model. A component of S can be obtained as $$S_{11} = \gamma \exp\left(\frac{1}{2} E_{Young}(E_{11})^2\right) E_{Young} E_{11}, \quad (14)$$

where $E_{Young}$ is Young's Modulus.

Equation (14) is an exponentially nonlinear soft tissue model that can be applied to breast. The two parameters, $\gamma$ and $E_{young}$, can be measured by experiment (Abbas and Donald, 2004, "A method to measure the hyperelastic parameters of ex vivo breast tissue samples", *Phys. Med. Biol.* 49, 4395-4405). Wellman ("Tactile Imaging,"*PhD dissertation*, Harvard University, 1999; hereby incorporated by reference in its entirety) developed a technique to measure the nonlinear elastic parameters of breast tissues using force-displacement data of thin slice tissues undergoing indentation experiment. The tissue samples tested were obtained during surgery and were tested immediately after removal from the body. Eight breast tissues (fatty, gland, phyllodes tumors, papilloma, lobular carcinoma, fibroadenoma, infiltrating ductal carcinoma, ductal carcinoma in situ) were tested and stress-train curves were obtained. The curves show that the mechanical properties between normal soft breast tissue and tumors are quite different. Tumors are stiffer than surround breast tissues and malignant tumors are much stiffer than benign ones.

Exponential hyperelastic models together with material parameters obtained from the Wellman (1999) experiments are used in simulations for testing the elastomammographic methods of the invention. Three materials are chosen: fatty tissue, glandular tissue and ductal carcinoma in situ. Elastic parameters are: λ35, μ=12.5, γ=0.4 for fatty tissue, λ=50, μ=25, γ=0.25 for glandular tissue, and λ=80, μ=35, γ=1.5 for ductal carcinoma in situ.

Figure 13:
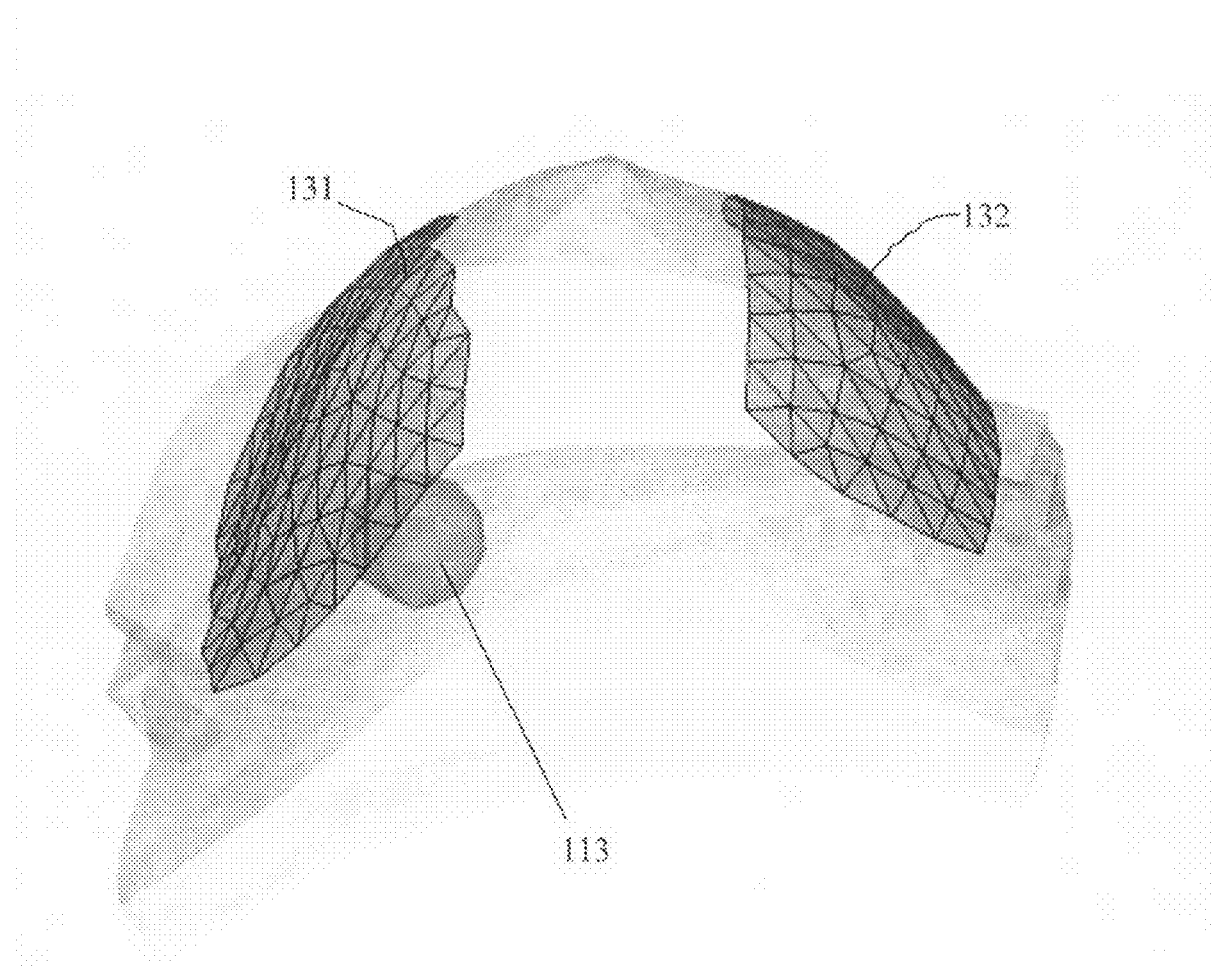
FIG. 13 shows a titled compression using paddles applied to the breast phantom.
Figure 14:
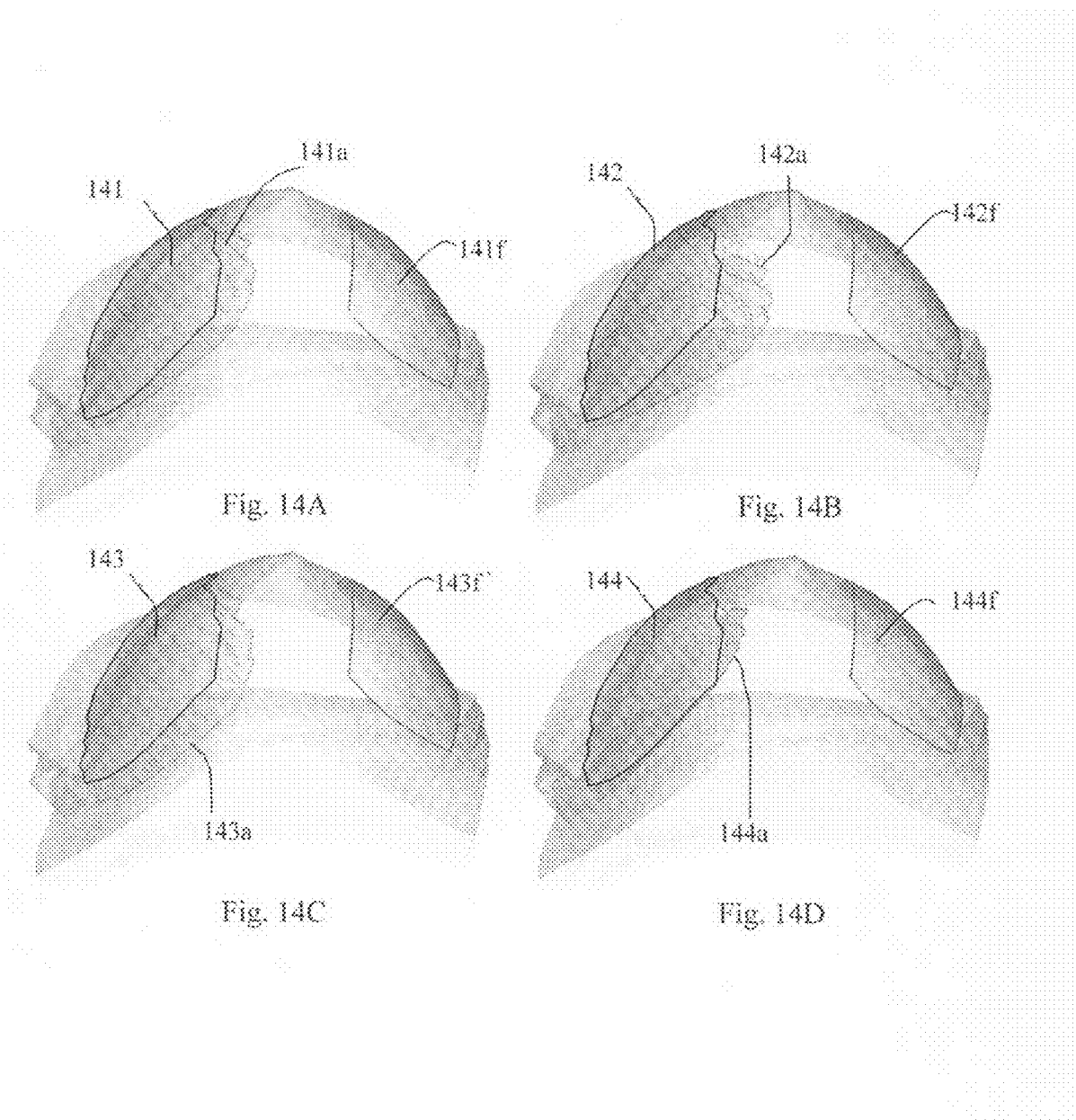
FIGS. 14A-14D show four types of compression loading.
Figure 15:
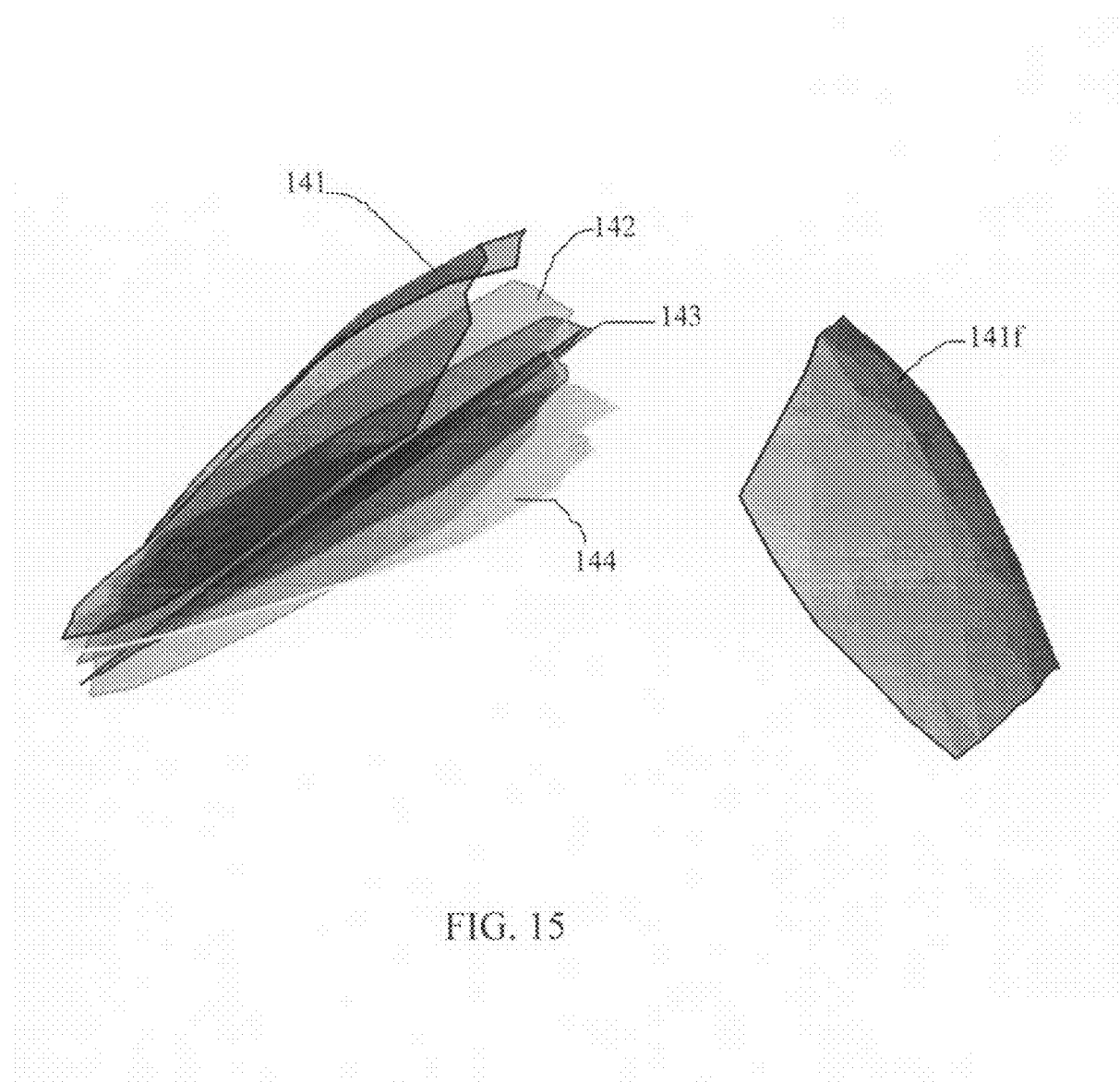
FIG. 15 illustrates the difference among the four types of compression loading.
Figure 16:
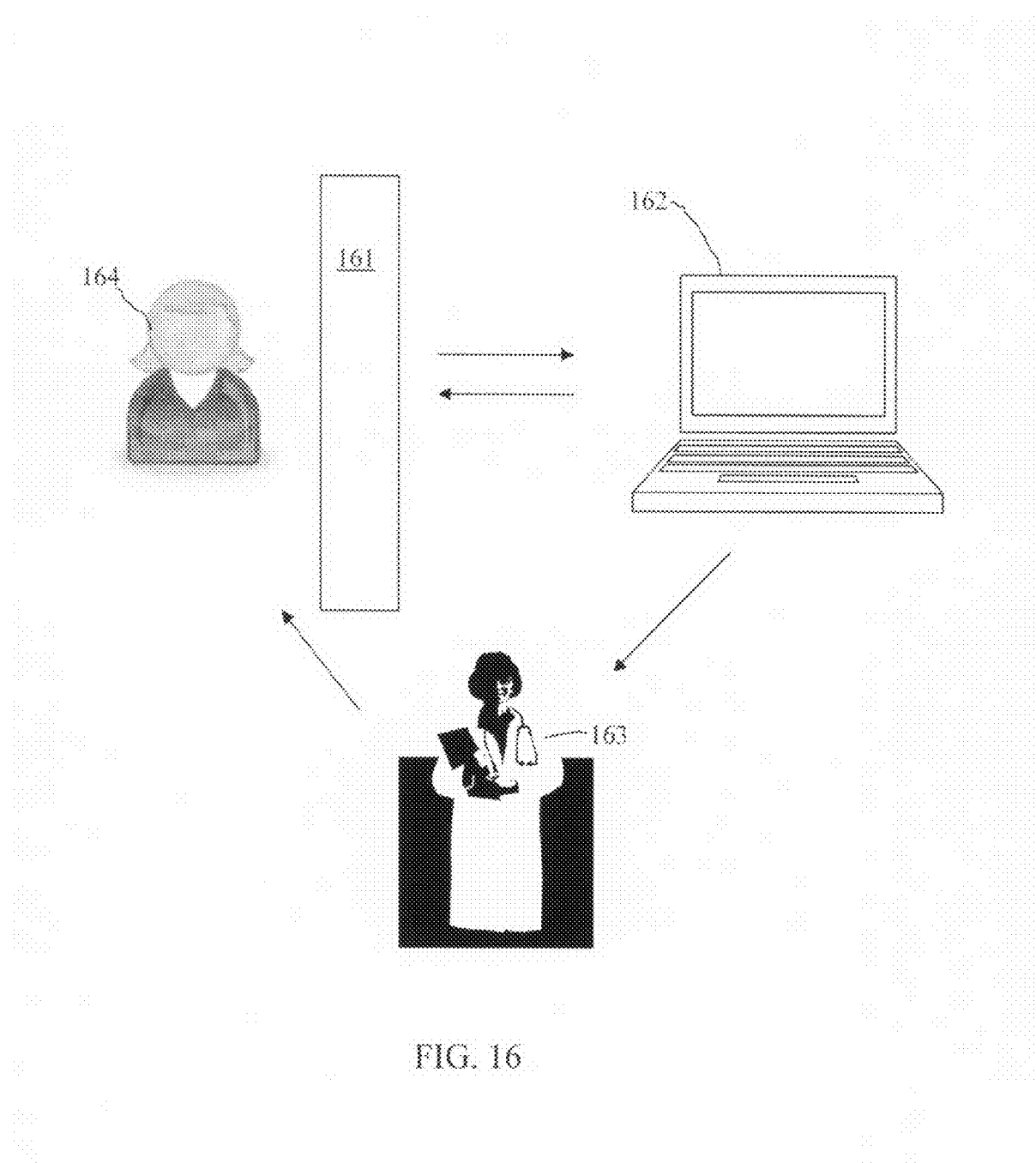
FIG. 16 is a block diagram of an apparatus in accordance with an embodiment of the invention in a clinical setting.

After the breast phantom and the material model are established, a forward problem is solved in which material parameters and external loading are given and deformation is solved. Displacements u=0 are prescribed on the base of phantom. Tilted compression by paddles is applied on upper surface of the breast phantom, as shown in FIG. 13. The paddle 131 close to the tumor 113 provides compression, and another paddle 132 is fixed during loading. Four types of compression loading with different angles are applied, as shown in FIGS. 14A-14D. Contours 141-144 represent paddle locations before loadings, contours 141a-144a represent those after loadings; and contours 141f-144f represent the corresponding fixed paddles. FIG. 15 further shows the comparison of paddle locations in the four loadings.

Using four sets of loading in forward problem can provide more information to reconstruct material parameters. Research has demonstrated that one set of measurements of the displacements and forces may not provide sufficient information of the reconstruction of modulus distribution. Using multiple sets of measurements, more deformation modes are simultaneously brought into consideration. The loadings should be close to tumors in order to make tumors have larger deformation. Reduction of the number of required loadings will increase the clinical efficiency and benefit the patients in terms of dose protocols. Thus, loadings with the richest stress/strain information are desired. The design of feasible loadings is important for success in clinical application of nonlinear elastography.

Given material parameters and loadings, the displacements and forces can be calculated. The surface force will be used as input to reconstruction material parameters in inverse problem. In fact, surface displacement and force are equivalent as input to solve inverse problem. Most of previous research uses displacement in linear elastography. In this nonlinear elastography study, it is found that the reconstruction is more sensitive to the force than to the displacement. Thus, surface force is measured and is compared with calculated force to reconstruct material parameters.

Reconstruction for nonlinear elastic moduli in 3-D breast phantom take input extracted from the deformation in response to the four loading modes shown in FIGS. 14A-14D. In each loading, the forces on surface nodes are measured as input. Initial guesses for material parameters are subsequently given. In this study, the same initial guesses are applied to three materials: λ=20, μ=10, γ=4. Therefore, surface force can be calculated based on initial guesses of material parameters. The error between calculated and measured force is used to obtain the objective function. Following the iterative optimization procedures (FIG. 10), gradients of the objective function are calculated, and material parameters are updated to arrive at the real values.

Elastic parameters used in the study include: λ=35, μ=12.5, γ=0.4 for fatty tissue, λ=50, μ=25, γ=0.25 for glandular tissue, and λ=80, μ=35, γ=1.5 for ductal carcinoma in situ.

Table 3 is the initial estimate and reconstructed results for nonlinear elastography. The results in the first part are based on ideal input. It is shown that the reconstructed results are very close to real values. The maximum error is 1.916% (λ for tumor), which is due to the effect of the tumor on surface force measurement being the smallest. A similar result exists also for linear elastography.

Elastography include forward and inverse problems. In a forward problem, which is used primarily for research purposes, material parameters and loadings are known and deformation is wanted. In an inverse problem, which is used clinically for screening and diagnostics purposes, external loadings and deformation are known and material parameters are wanted. The difficulty lies in how to calculate the gradient of the objective function efficiently and accurately. A straightforward calculation of gradients requires solving stiffness matrix in each iteration step, which takes most of the time consumed in the finite element method.

In accordance with an embodiment of the invention, an adjoint method is adopted to calculate gradients efficiently and accurately. Oberai et al. ("Solution of inverse problems in elasticity imaging using the adjoint method", *Inverse Problems*, 19, 297-313, 2003; hereby incorporated by reference in its entirety) adopted an adjoint method and proposed numerical scheme for reconstructing the nonuniform shear modulus in incompressible isotropic material using one component of the displacement field. Liu et al. (2005) applied this method for anisotropic material. In this study, this method is developed for nonlinear elastography. Advantages of the adjoint method result from solving two adjoint displacements in each iteration step, instead of the whole stiffness matrix, thus increasing the numerical efficiency significantly.

The impact of noise on reconstruction is also investigated for the nonlinear models. A 5% noise is applied to surface measurements, and the results are shown in the second part of Table 3. It can be seen that the reconstructions are far from the real values. The reason for this error in reconstruction is that the method seeks to find material parameters to minimize the objective function. When noise is present, a global minimum is not well defined. One way of overcoming this problem is to add a penalty term that provides an additional constraint on the solution space. The penalty term may push the solution into the right area of the solution space and minimize the resulting objective function.

A new objective function is defined as $$F = \Phi + \lambda \Pi, \tag{15}$$

where $\Phi$ is original objective function (Eq. (10)), $\lambda$ is a regularization factor, $\Pi$ is the penalty term. In accordance with an embodiment of the invention, an exponential form penalty term is applied:

$$\Pi = \sum_{k=1}^{K} (1 - \exp(-(\xi_k - a_k)^2)), \tag{16}$$

where K is the number of different material parameters, $\xi_k$ is a reconstructed elastic parameter, and $\alpha_k$ is the real parameter. When the real material parameters are unknown, $\alpha_k$ can be set as the most likely parameters.

The results are shown in the third part of Table 3. As shown, the regularization method significantly improves the reconstruction. Most of parameters are close to the real values. The largest error, which occurs for y in fatty tissue, is about 15%. The improvement results from that, by adding this penalty term, the reconstructed values are pulled from local minimum into a range close to real values.

For the regularization factor $\lambda$, a suitable factor should be tried in different scenarios. If there is a high confidence for the accuracy of experiment data, $\lambda$ should be smaller. On the other hand, if there is a high confidence that $\alpha_k$ is close to the exact value, $\lambda$ should be larger. For different types of materials, $\lambda$ may be different. As shown by Wellman (1999), the elastic parameters in fatty and glandular tissues are stable, as compared with those in tumors. Thus, a larger regularization factor λ may be used for fatty and glandular tissues while a smaller λ is used for tumors.

In Table 3, the same initial guesses are used (λ=20, μ=10, γ=1) for comparison. In practice, different initial guesses may be used for different materials. The initial guess close to real value can greatly improve the accuracy of reconstruction and shorten the iteration time.

TABLE 3

Initial estimate and reconstructed results for nonlinear elastogrpahy. The results in the first part are based on ideal input (without noise). The second part is based on an input with a 5% noise without regularization. The third part is based on input with 5% noise and regularization is applied to reduce the impact of noise.

|  | Fatty | | | Glandular | | | Tumor | | |
| --- | --- | --- | --- | --- | --- | --- | --- | --- | --- |
|  | λ | μ | γ | λ | μ | γ | λ | μ | γ |
| Real | 35 | 12.5 | 0.4 | 50 | 25 | 0.25 | 80 | 35 | 1.5 |
| Gues | 20 | 10 | 1 | 20 | 10 | 1 | 20 | 10 | 1 |
| | | | | Ideal Input | | | | | |
| Recon | 34.9988 | 12.5004 | 0.3999 | 50.0512 | 24.9998 | 0.2498 | 81.5331 | 34.9423 | 1.5003 |
| | | | | 5% Noise, Without Regularization | | | | | |
| Recon | 22.2753 | 8.4147 | 1.5038 | 56.1970 | 21.5414 | 0.2509 | 0.0001 | 41.5562 | 2.0010 |
| | | | | 5% Noise, With Exponential Form Regularization | | | | | |
| Recon | 37.5629 | 12.48318 | 0.4592 | 50.0014 | 25.0042 | 0.2444 | 80.0002 | 39.1539 | 1.5020 |

An elastomammographic apparatus in accordance with embodiments of the invention may include a conventional mammography device 161 and a computer 162. The computer 162 is loaded with a software package for image processing and for calculating the tissue stiffness properties using methods of the invention. In a clinical setting, a doctor 163 prescribes a mammography of a patient 164. The mammographic images are input to the computer 162 for processing, including building a finite-element mesh and iterative calculations shown in FIGS. 1 and 10. Alternatively, digitization and discretization of the mammography images may be performed in a separate computer.

Based on the calculations, the computer 162 outputs a suggestion, e.g., whether a suspected tumor is malignant or benign based on predetermined criteria, to the doctor 163. The doctor 163 may prescribe further mammographic projections to the patient 164 if needed.

The mammography imaging processing and the iterative calculations of the stiffness properties of the tissue may be included in a software package stored in a computer readable medium, such as computer memory, hard drive, compact disk, floppy disk, magnetic tape, flash memory, etc.

Advantageously, elastomammography in accordance with embodiments of the invention provides noninvasive, cost-effective methodology for characterization, differentiation, and follow-up of breast cancers. The techniques can be easily implemented on a desktop computer, which can be coupled with any digital mammographic devices. Hence, the healthcare benefits would be enormous.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

The words used in this specification to describe the invention and its, various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in must be understood as being generic to all possible meanings supported by the specification and by the word itself.

The definitions of the words or elements of the following invention and its various embodiments are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the invention and its various embodiments below or that a single element may be substituted for two or more elements in a claim.

Insubstantial changes from the claimed subject matter as viewed by a person with ordinary skill in the art, now known or later devised, are expressly contemplated as being equivalently within the scope of the invention and its various embodiments. Therefore, obvious substitutions now or later known to one with ordinary skill in the art are defined to be within the scope of the defined elements.

The invention and its various embodiments are thus to be understood to include what is specifically illustrated and described above, what is conceptionally equivalent, what can be obviously substituted and also what essentially incorporates the essential idea of the invention.

What is claimed is:

1. A method for obtaining a three-dimensional distribution of a stiffness property in breast tissue from mammographic images, comprising:
    applying a plurality of loadings to the breast tissue;
    obtaining a plurality of two-dimensional (2-D) imaging projections of the breast tissue from different directions;
    measuring from at least one of the plurality of 2-D imaging projections a force resulting from one of the plurality of loadings;
    measuring from at least one of the plurality of 2-D imaging projections a displacement of the breast tissue in response to the force;
    obtaining an initial set of input parameters for an estimation of the stiffness property of the breast tissue; and solving iteratively using the measured force and measured displacement from at least one of the plurality of 2-D imaging projections and the initial set of input parameters to create a three-dimensional distribution of the stiffness property of the breast tissue using a computer.

2. The method of claim 1, further comprising outputting a suggestion for tumor characterization in the breast tissue based on the iteratively-solved stiffness property.

3. The method of claim 1, further comprising obtaining a finite-element mesh for the breast tissue.

4. The method of claim 1, further comprising measuring an external surface of the breast tissue in a reconstructed undeformed state using images obtained from a three-dimensional camera.

5. The method of claim 1, wherein solving iteratively using the measured force and measured displacement from at least one of the plurality of 2-D imaging projections and the initial set of input parameters to create a three-dimensional distribution for the stiffness property comprises solving for a Lamé parameter, an elastic modulus, a Poisson ratio, or a contrast ratio.

6. The method of claim 1, wherein obtaining a plurality of two-dimensional (2-D) imaging projections comprises X-ray imaging or infrared imaging.

7. The method of claim 1, wherein obtaining a plurality of two-dimensional (2-D) imaging projections comprises imaging using X-ray mammography.

8. The method of claim 1, wherein solving iteratively for the three-dimensional distribution of the stiffness property of the breast tissue using a computer comprises:
   solving for an external force from the measured displacement;
   comparing the solved external force with the measured force;
   calculating an objective function;
   comparing the calculated objective function with a predetermined threshold; and
   if the calculated objective function is smaller than the predetermined threshold, outputting the stiffness property.

9. The method of claim 8 further comprising:
   determining if the calculated objective function is larger than the predetermined threshold and if so, then comprising:
   calculating an adjoint field;
   calculating gradients of the objective function; and
   updating the initial set of input parameters based on the calculated gradients.

10. The method of claim 1, wherein solving iteratively for the three-dimensional distribution of the stiffness property of the breast tissue using a computer comprises:
    solving a displacement from the measured force;
    comparing the solved displacement with the measured displacement;
    calculating an objective function;
    comparing the calculated objective function with a predetermined threshold; and
    if the calculated objective function is smaller than the predetermined threshold, outputting the stiffness property.

11. The method of claim 10 further comprising:
    determining if the calculated objective function is larger than the predetermined threshold and if so, then comprising:
    calculating an adjoint field;
    calculating gradients of the objective function; and
    updating the initial set of input parameters based on the calculated gradients.

12. The method of claim 1, wherein measuring from at least one of the plurality of 2-D imaging projections a displacement of the breast tissue in response to the force comprises measuring the displacement from a plurality of vertexes.

13. The method of claim 12, wherein measuring the displacement from the plurality of vertexes comprises measuring from the plurality of vertexes in an undeformed state assumed to remain as vertexes in a deformed state.

* * * * *